US007868040B2

(12) United States Patent
Wilson et al.

(10) Patent No.: US 7,868,040 B2
(45) Date of Patent: Jan. 11, 2011

(54) ANTI-CANCER COMBINATIONS

(75) Inventors: William R. Wilson, Waiuku (NZ); Bronwyn G. Siim, Auckland (NZ)

(73) Assignee: Cancer Research Technology Limited, London (GB)

( * ) Notice: Subject to any disclaimer, the term of this patent is extended or adjusted under 35 U.S.C. 154(b) by 149 days.

(21) Appl. No.: 11/830,659

(22) Filed: Jul. 30, 2007

(65) Prior Publication Data
US 2008/0070848 A1 Mar. 20, 2008

Related U.S. Application Data

(63) Continuation of application No. 10/790,943, filed on Mar. 2, 2004.

(30) Foreign Application Priority Data

Sep. 3, 2001 (GB) ................................. 0121285.1
Sep. 3, 2002 (WO) ..................... PCT/GB02/04025

(51) Int. Cl.
*A61K 31/335* (2006.01)
*A61K 31/26* (2006.01)
(52) U.S. Cl. ........................ 514/449; 514/492; 514/451; 514/453; 514/454; 424/649
(58) Field of Classification Search ................. 514/449, 514/492, 451, 453, 454; 553/136; 424/649
See application file for complete search history.

(56) References Cited

U.S. PATENT DOCUMENTS

| 3,678,077 | A | | 7/1972 | Nakanishi et al. |
| 4,565,806 | A | * | 1/1986 | Setala ..................... 514/54 |
| 4,602,034 | A | | 7/1986 | Briet et al. |
| 4,704,355 | A | | 11/1987 | Bernstein |
| 5,126,129 | A | | 6/1992 | Wiltrout et al. |
| 5,281,620 | A | | 1/1994 | Denny et al. |
| 5,464,826 | A | | 11/1995 | Grindey et al. |
| 5,620,875 | A | | 4/1997 | Hoffman et al. |

(Continued)

FOREIGN PATENT DOCUMENTS

DE 2015265 A1 10/1970

(Continued)

OTHER PUBLICATIONS

Calabresi et al, Goodman and Gilman's, The pharmacological basis of therapeutics, 9th edition, 1995.*

(Continued)

*Primary Examiner*—Ardin Marschel
*Assistant Examiner*—Savitha Rao
(74) *Attorney, Agent, or Firm*—Nelson Mullins Riley & Scarborough LLP; Brian C. Trinque

(57) ABSTRACT

The present invention relates to synergistic combinations of the compound 5,6-dimethylxanthenone-4-acetic acid (DMXAA) and an alkylating agent, which has anti-tumour activity. Preferably, the present invention relates to synergistic combinations of the compound 5,6-dimethylxanthenone-4-acetic acid (DMXAA) and cyclophosphamide. More particularly, the invention is concerned with the use of such combinations in the treatment of cancer and pharmaceutical compositions containing such combinations. The invention further provides for methods of preparing the combinations of the invention.

3 Claims, 2 Drawing Sheets

U.S. PATENT DOCUMENTS

| | | | |
|---|---|---|---|
| 5,817,684 | A | 10/1998 | Fleisch et al. |
| 5,863,904 | A | 1/1999 | Nabel et al. |
| 5,910,505 | A | 6/1999 | Fleisch et al. |
| 6,174,873 | B1 | 1/2001 | Wrenn |
| 6,194,454 | B1 | 2/2001 | Dow |
| 6,667,337 | B2 | 12/2003 | Wilson |
| 6,806,257 | B1 | 10/2004 | Lee et al. |
| 2001/0041713 | A1 | 11/2001 | Waldstreicher et al. |
| 2003/0003092 | A1 | 1/2003 | Krissansen et al. |
| 2004/0087611 | A1 | 5/2004 | Baguley et al. |
| 2004/0204480 | A1 | 10/2004 | Wilson et al. |
| 2005/0131059 | A1 | 6/2005 | Wang et al. |
| 2006/0009505 | A1 | 1/2006 | Baguley et al. |
| 2007/0060637 | A1 | 3/2007 | Wilson et al. |
| 2007/0082937 | A1 | 4/2007 | Baguley et al. |
| 2008/0070847 | A1 | 3/2008 | Wilson et al. |
| 2008/0070849 | A1 | 3/2008 | Wilson et al. |
| 2008/0070886 | A1 | 3/2008 | Wilson et al. |

FOREIGN PATENT DOCUMENTS

| | | | |
|---|---|---|---|
| DE | 19721211 | A1 | 11/1998 |
| EP | 0278176 | A2 | 8/1988 |
| EP | 0326149 | A2 | 8/1989 |
| EP | 0385467 | A1 | 9/1990 |
| EP | 0488718 | A2 | 6/1992 |
| EP | 0551200 | A1 | 7/1993 |
| EP | 0743064 | | 11/1996 |
| EP | 0584001 | B1 | 5/1997 |
| GB | 0121285.1 | | 9/2001 |
| GB | 0206839.3 | | 5/2002 |
| GB | 0225508.1 | | 11/2002 |
| GB | 0604114.9 | | 3/2006 |
| GB | 0157387.7 | | 8/2006 |
| GB | 0517386.9 | | 8/2006 |
| JP | 09040690 | A2 | 2/1997 |
| JP | 2001247459 | | 9/2001 |
| NZ | 336259 | | 6/1999 |
| NZ | 506060 | | 7/2000 |
| RU | 99121332 | A1 | 7/2001 |
| RU | 2195946 | C2 | 1/2003 |
| WO | WO 91/04014 | | 4/1991 |
| WO | WO 94/23753 | A1 | 10/1994 |
| WO | WO 95/09621 | A1 | 4/1995 |
| WO | WO 96/32418 | A1 | 10/1996 |
| WO | WO 96/36347 | A1 | 11/1996 |
| WO | WO 97/04761 | A1 | 2/1997 |
| WO | WO 97/34482 | A1 | 9/1997 |
| WO | WO 98/25600 | A1 | 6/1998 |
| WO | WO 98/25615 | A1 | 6/1998 |
| WO | WO 98/25616 | A1 | 6/1998 |
| WO | WO 98/42332 | A1 | 10/1998 |
| WO | WO 98/42334 | A1 | 10/1998 |
| WO | WO 98/42335 | A1 | 10/1998 |
| WO | WO 98/42336 | A1 | 10/1998 |
| WO | WO 98/42337 | A1 | 10/1998 |
| WO | WO 98/42345 | A1 | 10/1998 |
| WO | WO 98/42346 | A1 | 10/1998 |
| WO | WO 98/42650 | A2 | 10/1998 |
| WO | WO 00/10600 | A3 | 3/2000 |
| WO | WO 00/15176 | | 3/2000 |
| WO | WO 00/16798 | A1 | 3/2000 |
| WO | WO 00/48591 | A1 | 8/2000 |
| WO | WO 00/76497AI | | 12/2000 |
| WO | WO 01/34135 | A2 | 5/2001 |
| WO | WO 01/34137 | A2 | 5/2001 |
| WO | WO 01/34197 | A2 | 5/2001 |
| WO | WO 01/34198 | A2 | 5/2001 |
| WO | WO 02/09700 | A1 | 2/2002 |
| WO | WO 03/020259 | A2 | 3/2003 |
| WO | WO 03/080044 | | 10/2003 |
| WO | WO 2004/039363 | | 5/2004 |
| WO | WO 2005/027974 | A1 | 3/2005 |
| WO | WO 2007/023302 | | 3/2007 |
| WO | WO 2007/023307 | | 3/2007 |
| WO | WO 2009/053681 | | 4/2009 |

OTHER PUBLICATIONS

Siemann et al., abstract only, # 3344, Proceedings of the American Association for Cancer Research, 2000, vol. 41, p. 525.*

Calabresi et al (Chemotherapy of Neoplastic diseases, Section XII, pp. 1217-1218 Goodman and Gillman, The pharmacological basis of therapeutics, Eighth edition1990Siemann et al., abstract only, # 3344, Proceedings of the American Association for Cancer Research, 2000, vol. 41, p. 525.*

U.S. Appl. No. 12/064,632, filed Aug. 28, 2006, Green, et al.

U.S. Appl. No. 12/064,633, filed Aug. 25, 2006, Green, et al.

Aitken, et al.; "Synthesis and Antitumour Activity of New Derivatives of Flavone-8-acetic Acid (FAA), Part 4: Variation of the Basic Structure"; Arch. Pharm. Pharm. Med. Chem. (2000), 333(6):181-188.

Arbuck, et al.; "An Overview of Topoisomerase I—Targeting Agents"; Semin. Hematol. 1998, 35(3 supp.4):3-12.

Atwell, et al.; "Potential Antitumor Agents. 60. Relationships between Structure and in Vivo Colon 38 Activity for 5-Substituted 9-Oxoxanthene-4-acetic Acids"; J. Med. Chem. (1990), 33:1375-1379.

Atwell, et al.; "Synthesis and anti-tumor activity of topologically-related analogues of flavoneacetic acid"; Anti-Cancer Drug Design (1989), 4(2):161-169.

Avastin. Http://www.centerwatch.com/patient/drugs/dru851.html, Jun. 29, 2004.

Baguley, et al.; "Immunomodulatory Actions of Xanthenone Anticancer Agents"; BioDrugs; (1997), 8(2):119-127.

Baguley, et al.; "Mechanisms of Tumor Blood Flow Inhibition by The Antitumour Drug DMXAA (5,6-dimethylxanthenone-4-acetic acid"; Proceedings of the 11th NCI EORTC AACR Symposium; Copyright © 2000 Stichting NCI-EORTC Symposium on new drugs in cancer therapy; publ. By the AACR; Published as a Supplement to Clinical Cancer Research, vol. 6, Nov. 2000.

Baguley, et al.; Poster Abstract 138, of abstracts book for the 16th EORTC-NCI-AACR 2004 meeting on "Molecular Targets and Cancer Therapeutics"; Geneva, Switzerland (Sep. 28 to Oct. 1, 2004).

Baguley, et al.; "Potential of DMXAA combination therapy for solid tumors"; Expert Rev. Anticancer Ther. (2002), 2(5):593-603.

Baguley, et al.; "Serotonin involvement in the antitumour and host effects of flavone-8-acetic acid and 5, 6-dimethylxanthenone-4-acetic acid"; Cancer Chemother. Pharmacol (1993), 33(1):77-81.

Baguley, et al.; "Evidence that the 5-hydroxytryptamine antagonist, cyproheptadine, modulates nitric oxide production in mice in response to flavone acetic acid, vinblastine and other agents"; Biol. Nitric Oxide, Proc. Int. Meet.; Meeting Date 1991, vol. 2, (1992); 222-224.

Baguley, et al.; "Increased Plasma Serotonin Following Treatment With Flavone-8-Acetic Acid, 5,6-Dimethylxanthenone-4-Acetic Acid, Vinblastine, and Colchicine: Relation to Vascular Effects"; Oncology Research; (1997) 9(2), 55-60.

Barefoot, R.; "Speciation of platinum compounds: a review of recent applications in studies of platinum anticancer drugs"; Journal of Chromatography B (2001), 751:205-211.

Begley, et al.; "The Blood-Brain-Barrier: Principles for Targeting Peptides and Drugs to the Central Nervous System"; J. Pharm. Pharmacol. (1996), 48:136-146.

Bibby, et al.; "Flavone acetic acid—from laboratory to clinic and back"; Anti-Cancer Drugs (1993), 4:3-17.

Bibby, et al.; "Reduction of Tumor Blood Flow by Flavone Acetic Acid: A Possible Component of Therapy"; J. Natl. Cancer Inst. (1989), 81:216-220.

Brem, et al.; "Interstitial chemotherapy with drug polymer implants for the treatment of recurring gliomas"; J. Neurosurg. (1991), 74:441-446.

Browne, et al.; "Suppression of serum tumour necrosis factor-alpha by thalidomide does not lead to reversal of tumour vascular collapse and anti-tumour activity of 5, 6-dimethylxanthenone-4-acetic acid"; Anticancer Res. (1998), 18(6A):4409-4414.

Calabresi, et al.; "The Pharmacological Basis of Therapeutics, Ninth Edition," (1996), Goodman & Gilman's The Pharmacological Basis of Therapeutics. Section X, Chemotherapy of Neoplastic Diseases, pp. 1225-1229.

Cao, et al.; "Interferon-inducible Protein 10 Induction and Inhibition of Angiogenesis in Vivo by the Antitumor Agent 5, 6-Dimethylxanthenone-4-acetic Acid (DMXAA)"; Cancer Research (2001), 61(4):1517-1521.

Cao, et al.; "Thalidomide increases both intra-tumoural tumour necrosis factor-alpha production and anti-tumour activity in response to 5, 6-dimethylxanthenone-4-acetic acid"; Br. J. Cancer (1999), 80(5/6):716-723.

Chaplin, et al.; "Antivascular approaches to solid tumor therapy; evaluation of tubulin binding agents"; Proc. Annu. Meet. Am. Assoc. Cancer Res., Mar. 1996, vol. 37, #3009: 440-441 and Abstract.

Ching, et al.; "Antitumour responses to flavone-8-acetic acid and 5, 6-dimethylxanthenone-4-acetic acid in immune deficient mice"; Br. J. Cancer (1992), 66(1):128-130.

Ching, et al.; "Effect of Tumor Growth on the Macrophage Response to the Antitumour Agent 5,6-Dimethylxanthenone-4-acetic Acid"; Anticancer Research (1993), 13(6A):2069-2076.

Ching, et al.; "Haematological effects in mice of the antitumour agents xanthenone-4-acetic acid, 5, 6-dimethylxanthenone-4-acetic acid and flavoneacetic acid"; Cancer Chemother. Pharmacol. (1991), 28(6):414-419.

Ching, et al.; "In vitro Methods for Screening Agents with an Indirect Mechanism of Antitumour Activity: Xanthenone Analogues of Flavone Acetic Acid"; Eur. J. Cancer (1991), 27(12):1684-1689.

Ching, et al.; "Induction of Natural Killer Activity by Xanthenone Analogues of Flavone Acetic Acid: Relation with Antitumour Activity"; Eur. J. Cancer (1991), 27(1):79-83.

Ching, et al.; "Induction of STAT and NF-kappa-B Activation by the Antitumor Agents 5,6-Dimethylxanthenone-4-acetic Acid and Flavone Acetic Acid in a Murine Macrophage Cell Line"; Biochemical Pharmacology (1999), 58(7):1173-1181.

Ching, et al.; "Induction of Tumor Necrosis Factor-alpha Messenger RNA in Human and Murine Cells by the Flavone Acetic Acid Analogue 5, 6-Dimethylxanthenone-4-acetic acid"; Cancer Research (1994), 54(4):870-872.

Ching, et al.; "Stimulation of macrophage tumouricidal activity by 5, 6-dimethylxanthenone-4-acetic acid, a potent analogue of the antitumour agent flavone-8-acetic acid"; Biochemical Pharmacology (1992), 44(1):192-195.

Ching, et al.; "Effect of thalidomide on tumour necrosis factor production and anti-tumour activity induced by 5, 6-dimethylxanthenone-4-acetic acid"; Br. J. Cancer (1995), 72(2):339-343.

Ching, et al.; "Induction of intratumoral tumor necrosis factor (TNF) synthesis and hemorrhagic necrosis by 5, 6-dimethylxanthenone-4-acetic acid (DMXAA) in TNF knockout mice"; Cancer Res. (1999), 59(14):3304-3307.

Ching, et al.; "Interaction between endotoxin and the antitumour agent 5, 6-dimethylxanthenone-4-acetic acid in the induction of tumor necrosis factor and haemorrhagic necrosis of colon 38 tumors"; Cancer Chemother. Pharmacol. (1994), 35(2):153-160.

Ching, et al.; "Interaction of thalidomide, phthalimide analogues of thalidomide and pentoxifylline with the antitumour agent 5, 6-dimethylxanthenone-4-acetic acid: concomitant reduction of serum tumour necrosis factor-alpha and enhancement of antitumour activity"; Br. J. Cancer. (1998), 78(3):336-343.

Ching, et al.; "The Anti-Tumour and Immune-Modulatory Activites of Flavone Acetic and Xanthone Acetic Acids"; 1990; N.P. Das (ed.), flavanoids in Biology and Medicine III. Proceedings of the 3rd International Symposium on Flavonoids in Biology and Medicine; 381-391.

Cliffe, et al.; "Combining bioreductive drugs (SR 4233 or SN 23862) with the vasoactive agents flavone acetic acid or 5, 6-dimethylxanthenone acetic acid"; Int. J. Radiation Oncology Biol. Phys. (1994), 29(2):373-377.

Coloma, et al.; "Transport across the primate Blood-Brain-Barrier of a genetically engineered Chimeric Monoclonal Antibody to the Human Insulin Receptor"; Pharmaceutical Research (2000), 17(3):266-274.

Combretastatin Update 1: "In Ohio Phase 1 Trial, Some Tumors Respond, Patients Experience Vascular Stress"; PSA Rising; Medical Pike Briefs; Headline Index: Clinical Trial Phase 1 Results; Nov. 8, 1999.

Corbett, et al.; "Activity of flavone acetic acid (NSC-347512) against solid tumors of mice"; Investigational New Drugs (1986), 4:207-220.

Cusmano, et al.; "Rearrangement of 3-(N-Heteroarylamino)-1,2,5-Oxadiazoles: Triazolo[1,5-a]Quinolines and Triazolo[1,5-a]Pyridines"; Heterocycles (1993), 36(7):1577-1588.

Djeha, et al.; "Synergistic in vivo antitumor activity in lung and colon cancer xenografts with the vascular disrupting agent DMXAA combined with bevacizumab"; Proc. Am. Assoc. Cancer. Res. Annual Meeting, (2006), 47:55.

Economou, et al.; "Tumour necrosis factor production by IL-2-activated macrophages in vitro and in vivo"; Immunology (1989), 67:514-519.

Everett, et al.; "Decarboxylation of the antitumour drugs flavone-8-acetic acid and xanthenone-4-acetic acid by nitrogen dioxide"; Anti-Cancer Drug Design (1994), 9(1):68-72.

Everett, et al.; "High-performance ion chromatography applied to free-radical mechanisms in drug design. The problem of ion analysis at high ionic strengths"; Journal of Chromatography A. (1997), 770(1/2):273-279.

Fujii, et al.; "Vaccination with B7-1 tumor and anti-adhesion therapy with RGD pseudo-peptide (FC-336) efficiently induce anti-metastatic effect"; Clinical & Experimental Metastasis (1998), 16:141-148.

Futami, et al.; "Cytokine induction and therapeutic synergy with interleukin-2 against murine renal and colon cancers by xanthenone-4-acetic acid derivatives"; J. Immunother. (1992), 12(4):247-255.

Galbraith, et al.; "Effects of 5,6-Dimethylxanthenone-4-acetic acid on Human Tumor Microcirculation Assessed by Dynamic Contrast-enhanced Magnetic Resonance Imaging"; J. Clinical Oncology (2002), 20(18):3826-3840.

Gamage, et al.; "Structure-activity relationships for substituted 9-oxo-9,10-dihydroacridine-4-acetic acids: analogues of the colon tumour active agent xanthenone-4-acetic acid"; Anti-Cancer Drug Design; (1992), 7(5):403-414.

Graham, et al.; Fresh from the Pipeline: Cetuximab; Nature Reviews Drug Discovery (2004), 3:549-550.

Griffioen, et al.; "Angiogenesis Inhibitors Overcome Tumor Induced Endothelial Cell Anergy"; Int. J. Cancer (1999), 80:315-319.

Hill, et al.; "Anti-Vascular Approaches to Solid Tumour Therapy: Evaluation of Vinblastine and Flavone Acetic Acid"; Int. J. Cancer (1995), 63(1):119-123.

Hornung, et al.; "Augmentation of Natural Killer Activity, Induction of IFN and Development Tumor Immunity During the Successful Treatment of Established Murine Renal Cancer Using Flavone Acetic Acid and IL-2"; The Journal of Immunology (1988), 141(10):3671-3679.

Jameson, et al.; "Clinical aspects of a phase I trial of 5,6-dimethylxanthenone-4-acetic acid (DMXAA), a novel antivascular agent"; British Journal of Cancer (2003), 88:1844-1850.

Jameson, et al.; "Phase I Pharmacokinetic and Pharmacodynamic Study of 5,6-Dimethylxanthenone-4-Acetic Acid (DMXAA), A Novel Antivascular Agent"; Proc. Am. Soc. Clin Oncol. (2000), 19: 182a.

Johnson, et al.; "Relationships between drug activity in NCI preclinical in vitro and in vivo models and early clinical trials"; British J. of Cancer (2001), 84(10):1424-1431.

Joseph, et al.; "Stimulation of Tumors to Synthesize Tumor Necrosis Factor-alpha in Situ Using 5,6-Dimethylxanthenone-4-acetic Acid: A Novel Approach to Cancer Therapy"; Cancer Res. (1999), 59(3):633-638.

Kanwar, et al.; "Taking lessons from dendritic cells: Multiple xenogeneic ligands for leukocyte integrins have the potential to stimulate anti-tumor immunity"; Gene Therapy (1999), 6:1835-1844.

Kanwar, et al.; "Vascular attack by 5, 6-dimethylxanthenone-4-acetic acid combined with B7.1 (CD80)-mediated immunotherapy overcomes immune-resistance and leads to the eradication of large tumors and multiple tumor foci"; Cancer Res. (2001), 61(5):1948-1956.

Kelland, L.; "Targeting Established Tumor Vasculature: A Novel Approach to Cancer Treatment"; Curr.Cancer. Ther. Rev. (2005), 1(1):1-9.

Kestell, et al.; "Determination of xanthenone-4-acetic acid in mouse plasma by high-performance liquid chromatography"; J. Chromatography (1991), 564(1):315-321.

Kestell, et al.; "Disposition of the novel antitumour agent xanthenone-4-acetic acid in the mouse: identification of metabolites and routes of elimination"; Xenobiotica (1994), 24(7):635-647.

Kestell, et al.; "Plasma disposition, metabolism and excretion of the experimental antitumour agent 5,6-dimethylxanthenone-4-acetic acid in the mouse, rat and rabbit"; Cancer Chemother. Pharmacol. (1999), 43(4):323-330.

Kestell, et al.; "Modulation of the pharmacokinetics of the antitumour agent 5,6-dimethylxanthenone-4-acetic acid (DMXAA) in mice by thalidomide"; Cancer Chemother. Pharmacol (2000), 46(2):135-141.

Kroll, et al.; "Improving Drug Delivery to Intracerebral Tumor and Surrounding Brain in a Rodent Model: A Comparison of Osmotic versus Bradykinin Modification of the Blood-Brain and/or Blood-Tumor Barriers"; Neurosurgery (1998), 43(4):879-886.

Langer, R.; "New Methods of Drug Delivery"; Science (1990), 249:1527-1533.

Lash, et al.; "Enhancement of the anti-tumour effects of the antivascular agent 5,6-dimethylxanthenone-4-acetic acid (DMXAA) by combination with 5-hydroxytryptamine and bioreductive drugs"; Br. J. Cancer (1998), 78(4):439-445.

Laws, et al.; "Preclinical in vitro and in vivo activity of 5,6-dimethylxanthenone-4-acetic acid"; British Journal of Cancer; (1995), 71(6):1204-1209.

Lissoni, et al.; "Neuroimmunotherapy of advanced solid neoplasms with simgle evening subcutaneous injection of low-dose interleukin-2 and melatonin: Preliminary results"; European Journal of Cancer (1993), 29A(2):185-189.

Maier, et al.; "In-Vitro inhibition of endothelial cell growth by the antiangiogenic drug AGM-1470 (TNP-470) and the anti-endoglin antibody TEC-11"; Anti-Cancer Drugs (1997), 8:238-244.

Marnett, L.J.; "Aspirin and Related Nonsteroidal Anti-inflammatory Drugs as Chemopreventive Agents against Colon Cancer"; Preventive Medicine 24,103-106 (1995).

Marona, H.; "Synthesis and Properties of Some Xanthone-2-Alkylcarboxylic acids and Xanthone-2-Glyoxal"; Polish Journal of Chemistry, 54:2059 (1980).

McKeage, et al.; "5,6-Dimethylxanthenone-4-Acetic Acid in the Treatment of Refractory Tumors: a Phase I Safety Study of a Vascular Disrupting Agent"; Clin. Cancer Res. (2006), 12(6):1776-1784.

McKeage, et al.; "Plasma pharmacokinetics of the antitumour agents 5,6-dimethylxanthenone-4-acetic acid, xanthenone-4-acetic acid and flavone-8-acetic acid in mice"; Cancer Chemother. Pharmacol.; (1991) 28(6), 409-413.

McLachlan, et al.; "The Potential of Cyclosporin A as an Anti-Tumour Agent"; Int. J. Immun. (1990), 12(5):469-479.

Miners, et al.; "Preclinical Prediction of Factors Influencing the Elimination of 5,6-Dimethylxanthenone-4-acetic Acid, a New Anticancer Drug"; Cancer Research (1997), 57(2):284-289.

Moilanen, et al.; "Persistent induction of nitric oxide synthase in tumours from mice treated with the anti-tumour agent 5, 6-dimethylxanthenone-4-acetic acid"; British Journal of Cancer (1998), 77(3): 426-433.

Murata, et al.; "Comparative effects of combretastatin A-4 disodium phosphate and 5, 6-dimethylxanthenone-4-acetic acid on blood perfusion in a murine tumour and normal tissues"; Int. J. Radiat. Biol. (2001), 77(2):195-204.

Nakamura, et al.; "Antitumor Effect of Recombinant Human Interleukin 1 Alpha against Murine Syngeneic Tumors"; Jpn. J. Cancer Research (Gann) (1986), 77:767-773.

Nakanishi, et al.; "Carboxylic Acids"; Chem. Abstr. 76:126784w (1972), (Abstract of Japan A-7,200,425).

Nakanishi, et al.; "Studies of Anti-Inflammatory Agents XXXI; Studies on the Synthesis and Anti-Inflammatory Activity of Xanthenyl- and Benzo-pyranopyridinylacetic acid Derivatives"; Yakugaku Zasshi (1976), 96:99-109.

Nawrocki, et al.; "Genetically modified tumour vaccines—where we are today"; Cancer Treatment Reviews (1999), 25:29-46.

Neuwelt, et al.; "Increased Delivery of Tumor-specific Monoclonal Antibodies to Brain after Osmotic Blood-Brain-Barrier modification in Patients with Melanoma Metastatic to the Central Nervous System"; Neurosurgery (1987), 20(6):885-895.

Nishino, et al.; "Oxidation of 9-Xanthenones with Lead (IV) Acetate. Formation of Di-gamma-lactones"; Bull. Chem Soc. Jpn. (1983), 56:2847-48.

Nishino, et al.; "Regioselective Carboxylation of 9-Xanthenones with Manganese (III) Acetate." Bull. Chem Soc. Jpn. (1983), 56:474-480.

O'Reilly, et al.; "Endostatin: An Endogenous Inhibitor of Angiogenesis and Tumor Growth"; Cell (1997), 88:277-285.

Pang, et al.; "Antitumour Activity of the Novel Immune Modulator 5, 6-Dimethylxanthenone-4-acetic Acid (DMXAA) in Mice Lacking the Interferon-gamma Receptor"; European Journal of Cancer (1998), 34(8):1282-1289.

Patel, et al.; "The Effect of 5, 6-Dimethylxanthenone-4-acetic acid on Tumour Necrosis Factor Production by Human Immune Cells"; Anticancer Research (1997), 17(1A):141-150.

Peckham, et al.; "Oxford Textbook of Oncology". Oxford University Press, vol. 1. p. 451, 1995.

Pedley, et al.; "Ablation of Colorectal Xenografts with Combined Radioimmunotherapy and Tumor Blood Flow-modifying Agents"; Cancer Research (1996), 56(14):3293-3300.

Pedley, et al.; "Enhancement of Radioimmunotherapy by Drugs Modifying Tumour Blood Flow in a Colonic Xenograft Model"; Int. J. Cancer (1994), 57(6):830-835.

Pedley, et al.; "Enhancement of antibody-directed enzyme prodrug therapy in colorectal xenografts by an antivascular agent"; Cancer Res. (1999), 59(16):3998-4003.

Perera, et al.; "Activation of LPS-Inducible Genes by the Antitumor Agent 5,6-Dimethylxanthenone-4-Acetic Acid in Primary Murine Macrophages"; The Journal of Immunology (1994), 153(10):4684-4693.

Phillips, R.M.; "Inhibition of DT-diaphorase (NAD(P)H:quinone oxidoreductase, EC 1.6.99.2) by 5,6-dimethylxanthenone-4-acetic acid (DMXAA) and flavone-8-acetic acid (FAA): Implications for bioreductive drug development"; Biochem. Pharmacol. (1999), 58(2):303-310.

Philpott, et al.; "Induction of tumor necrosis factor-alpha by single and repeated doses of the antitumour agent 5, 6-dimethylxanthenone-4-acetic acid"; Cancer Chemother. Pharmacol. (1995), 36(2):143-148.

Philpott, et al.; "Production of tumour necrosis factor-alpha by cultured human peripheral blood leukocytes in response to the anti-tumour agent 5, 6-dimethylxanthenone-4-acetic acid (NSC 640488)"; British Journal of Cancer (1997), 76(12):1586-1591.

Plowman, et al.; "Flavone Acetic Acid: A Novel Agent with Preclinical Antitumor Activity Against Colon Adenocarcinoma 38 in Mice"; Cancer Treatment Reports (1986), 70(5):631-635.

Pruijn, et al.; "Mechanisms of enhancement of the antitumour activity of melphalan by the tumour-blood-flow inhibitor 5, 6-dimethylxanthenone-4-acetic acid"; Cancer Chemother. Pharmacol. (1997), 39(6):541-546.

PTCL. Chemical and Other Safety Information. "ptcl.chem.ox.ac.uk/MSDS".

Rewcastle, et al.; "Light-Induced Breakdown of Flavoneacetic Acid and Xanthenone Analogues in Solution"; J. Natl. Cancer Inst. (1990), 82(6):528-529.

Rewcastle, et al.; "Potential Antitumor Agents. 58. Synthesis and Structure-Activity Relationships of Substituted Xanthenone-4-acetic Acids Active against the Colon 38 Tumor in Vivo"; J. Med. Chem. (1989), 32(4):793-799.

Rewcastle, et al.; "Potential Antitumor Agents. 61. Structure-Activity Relationships for in Vivo Colon 38 Activity among Disubstituted 9-oxo-9H-xanthene-4-acetic Acids"; J. Med. Chem. (1991), 34(1):217-222.

Rewcastle, et al.; "Potential Antitumor Agents. 62. Structure-Activity Relationships for Tricyclic Compounds Related to the Colon Tumor Active Drug 9-Oxo-9H-xanthene-4-acetic Acid"; J. Med. Chem. (1991), 34:491-496.

Rewcastle, et al.; "Potential Antitumor Agents. 63. Structure-Activity Relationships for Side-Chain Analogues of the Colon 38 Active Agent 9-oxo-9H-xanthene-4-acetic Acid"; J. Med. Chem. (1991), 34(9):2864-2870.

Rewcastle, G. W.; "Synthesis and Development of Two New Classes of Anticancer Drugs: the tricyclic Carboxamides and the xanthenoneacetic acids"; Chemistry in New Zealand (1989), 53(6):145-150.

Rieckmann, et al.; "Okadaic Acid is a potent inducer of AP-1, NF-kappa-B, and Tumor-Necrosis Factor-alpha in Human B Lymphocytes"; Biochem. Biophys. Res. Commun. (1992), 187(1):51-57.

Rustin et al.; "5,6-Dimethylxanthenone-4-acetic acid (DMXAA), a novel antivascular agent: phase I clinical and pharmacokinetic study"; British Journal of Cancer (2003), 88:1160-1167.

Rustin et al.; "Impact on Tumour Perfusion Measured by Dynamic Magnetic Resonance Imaging (MRI), in the Phase 1 Trial of 5,6-dimethylxanthenone-4-aceticAcid (DMXAA)"; Proc. 10th NCI-EORTC Symp. New Drugs (1998), 10:126.

Rustin, G.; "Vascular Targeting in the Clinic"; Abstract; ICTR 2000: 1st Int'l Conference on Translational Research A., 2000.

Saltiel, E.; "Erlotinib". Http://www.medicinenet.com/erlotinib/article.htm. Nov. 28, 2004.

Saltiel, E.; "Gefitinib". Http://www.medicinenet.com/gefitinib/article.htm. Jun. 22, 2005.

Sausville, et al.; "Contributions of human tumor xenografts to anticancer drug development"; Cancer Research (2006), 66(7):3351-3354.

Shoemaker, et al.; "Pleiotropic Resistance and Drug Development"; Cancer Drug Resistance (1986), 143-149.

Showalter, H.; "Potential Antitumor Agents. 61. Structure-Activity Relationships for in Vivo Colon 38 Activity Among Disubstituted 9-Oxo-9H-xanthene-4-acetic acids"; Chemtracts: Org. Chem. (1991), 4(2): 168-171. Commentary of Rewcastle: J. Med. Chem. (1991), 34:217-222.

Siemann, et al.; "Enhanced Antitumor Efficacy through the combination of Vascular Targeting Agents and Conventional Anticancer Drugs"; Proceedings of the American Association for Cancer Research (2000), 41:525.

Siemann, et al.; "Vascular Targeting Agents Enhance Chemotherapeutic Agent Activities in Solid Tumor Therapy"; Int. J. Cancer (2002), 99:1-6.

Siim, et al.; "Marked potentiation of the antitumour activity of chemotherapeutic drugs by the antivascular agent 5,6-dimethylxanthenone-4-acetic acid (DMXAA)"; Cancer Chemother Pharmacol (2003), 51:43-52.

Siim, et al.; "Nitro Reduction as an Electronic Switch for Bioreductive Drug Activation"; Oncology Research (1997), 9(6/7):357-369.

Siim, et al.; "Scintigraphic Imaging of the Hypoxia Marker 99m-Technetium-labeled 2,2'-(1,4-Diaminobutane)bis(2-methyl-3-butanone) Dioxime (99mTc-labeled HL-91; Prognox): Noninvasive Detection of Tumor Response to the Antivascular Agent 5, 6-Dimethylxanthenone-4-acetic Acid"; Cancer Research (2000), 60(16):4582-4588.

Simone, et al.; "Oncology". Cecil Text Book of Medicine. 20th Edition vol. 1, W. B. Saunders Company. 1997, p. 1004-1010.

Temsamani, et al.; "Brain drug delivery technologies: novel approaches for transporting therapeutics"; Pharm. Sci. Technology Today (1998), 3(5):155-162.

Thomsen, et al.; "Evidence for the Production of Nitric Oxide by Activated Macrophages Treated with the Antitumor Agents Flavone-8-acetic Acid and Xanthenone-4-acetic Acid"; Cancer Research (1990), 50(21):6966-6970.

Thomsen, et al.; "Modulation of superoxide production from murine macrophages by the antitumour agent flavone acetic acid and xanthenone acetic acid analogues"; Biochemical Pharmacology (1992), 43(2):386-389.

Thomsen, et al.; "Nitric Oxide: its production in host-cell-infiltrated EMT6 spheroids and its role in tumor cell killing by flavone-8-acetic acid and 5, 6-dimethylxanthenone-4-acetic acid"; Cancer Chemother. Pharmacol. (1992), 31(2):151-155.

Thomsen, et al.; "Nitric Oxide Production in endotoxin-resistant C3H/HeJ mice stimulated with flavone-8-acetic acid and xanthenone-4-acetic acid analogues"; Biochem. Pharmacol. (1992), 43(11):2401-2406.

Thomsen, et al.; "Tumor-dependent increased plasma nitrate concentrations as an indication of the antitumor effect of flavone-8-acetic acid and analogues in mice"; Cancer Res. (1991), 51(1):77-81.

Thrash-Bingham, et al.; "aHIF: A natural antisense transcript overexpressed in human renal cancer during hypoxia"; The Journal of the National Cancer Institute (1999), 91(2):143-151.

Tyle, P.; "Iontophoretic Devices for Drug Delivery"; Pharmaceutical Research (1986), 3(6):318-326.

Van Der Auwera, et al.; "Conformational Features of Four Model Tripeptides Having Piv-Pro-MeXaa-NMe2 Sequences"; Bull. Soc. Chim. Belg. (1988), 97(3):199-207.

Van Moorsel, et al.; "Combination Chemotherapy Studies with Gemcitabine and Etoposide in Non-Small Cell Lung and Ovarian Cancer Cell Lines"; Biochemical Pharmacology (1999), 57:407-415.

Veszelovszky, et al.; "Flavone Acetic Acid and 5, 6-Dimethylxanthenone-4-acetic Acid: Relationship between Plasma Nitrate Elevation and the Induction of Tumour Necrosis"; Eur. J. Cancer, Part A (1993), 29A(3): 404-408.

Vincent, et al.; "Chemotherapy with DMXAA (5, 6-dimethylxanthenone-4-acetic acid) in combination with CI-1010 (1H-imidazole-1-ethanol, alpha-[[(2-bromoethyl)amino]methyl]-2-nitro-, mono-hydrobromide (R isomer)) against advanced stage murine colon carcinoma 26"; Oncology Reports (1997), 4(1):143-147.

Watts, et al.; "Changes in coagulation and permeability properties of human endothelial cells in vitro induced by TNF-alpha or 5,6 MeXAA"; British Journal of Cancer, Suppl. (1996), 74(27):S164-S167.

Webster, et al.; "Metabolism and Elimination of 5,6-Dimethylxanthenone-4-Acetic Acid in the Isolated Perfused Rat Liver"; Drug Metabolism and Disposition (1995), 23(3):363-368.

Westland, et al.; "Activated non-neural specific T cells open the blood-brain-barrier to circulating antibodies"; Brain (1999), 122:1283-1291.

Wiesenthal. "Is one 'sensitive' drug better than another? Can you detect drug synergy? What are the best drug combinations?" http://weisenthal.org/feedback.html, Feb. 4, 2002.

Wilkinson, et al.; "Tamoxifen (Noivadex*) Therapy—Radionale for Loading Dose Followed by Maintenance Dose for Patients with Metastatic Breast Cancer"; Cancer Chemotherapy Pharmacol. (1982), 10:33-35.

Wilson, et al.; "Combination of the Antivascular Agent DMXAA with Radiation and Chemotherapy", International Journal of Oncology, Biology and Physics (2000), 46(3):706, [abstract 46].

Wilson, et al.; "Enhancement of Tumor Radiation Response by the Antivascular Agent 5,6-Dimethylxanthenone-4-Acetic Acid"; Int. J. Radiation Oncology Biol. Phys. (1998), 42(4):905-908.

Wilson, et al.; "Tertiary amine N-oxides as bioreductive drugs: DACA N-oxide, nitracrine N-oxide and AQ4N"; British Journal of Cancer Supplemental (1996), 74(27):S43-S47.

Wilson, et al.; "Hypoxia-Activated Prodrugs as Antitumour Agents: Strategies for Maximizing Tumor Cell Killing"; Clinical and Experimental Pharmacology and Physiology (1995), 22(11):881-885.

Wouters, et al.; "Hypoxia as a target for combined modality treatments"; European J. Cancer (2002), 38:240-257.

Zaharko, et al.; "Therapeutic and Pharmacokinetic Relationships of Flavone Acetic Acid: An Agent with Activity Against Solid Tumors"; Cancer Treatment Reports (2002), 70(12):1415-1421.

Zaks-Zilberman, et al.; "Induction of Adrenomedullin mRNA and Protein by Lipopolysaccharide and Paclitaxel (Taxol) in Murine Macrophages"; Infection and Immunity (1998), 66(10):4669-4675.

Zhang, et al.; "Conjugation of brain-derived neurotrophic factor to a blood-brain-barrier resistant drug targeting system enables neuroprotection in reginal brain ischemia following intravenous injection of the neurotrophin"; Brain Research (2001), 889:49-56.

Zhao, et al.; "Effects of the serotonin receptor antagonist cyproheptadine on the activity and pharmacokinetics of 5, 6-dimethylxanthenone-4-acetic acid (DMXAA)"; Cancer Chemother. Pharmacol. (2001), 47(6):491-497.

Zhao, et al.; "Improvement of the antitumor activity of intraperitoneally and orally administered 5,6-dimethylxanthenone-4-acetic acid by optimal scheduling"; Clinical Cancer Research (2003), 9:6545-6550.

Zhao, et al.; "Oral activity and pharmacokinetics of 5,6-dimethylxanthenone acetic acid (DMXAA) in mice"; Cancer Chemother. Pharmacol. (2002), 49:20-26.

Zhou, et al.; "5,6-dimethylxanthenone-4-acetic acid (DMXAA): a new biological response modifier for cancer therapy"; Invest New Drugs. (2002), 20(3):281-95.

Zhou, et al.; "Determination of the covalent adducts of the novel anti-cancer agent 5, 6-dimethylxanthenone-4-acetic acid in biological samples by high-performance liquid chromatography"; J. Chromatography B (2001), 757:343-348.

Zhou, et al.; "Determination of unbound concentration of the novel anti-tumour agent 5,6-dimethylxanthenone-4-acetic acid in human plasma by ultrafiltration followed by high-performance liquid chromatography with fluorimetric detection"; J. Chromatography B (2001), 757(2):359-363.

Zhou, et al.; "Effects of anticancer drugs on the metabolism of the anticancer drug 5,6-dimethylxanthenone-4-acetic acid (DMXAA) by human liver microsomes"; J. Clin. Pharmacol. (2001), 52:129-136.

Zhou, et al.; "Reversible binding of the novel anti-tumour agent 5,6-dimethylxanthenone-4-acetic acid to plasma proteins and its distribution into blood cells in various species"; J. Pharmacy Pharmacology (2001), 53(4):463-471.

Zhou, et al.; "A difference between the rat and mouse in the pharmacokinetic interaction of 5, 6-dimethylxanthenone-4-acetic acid with thalidomide"; Cancer Chemother. Pharmacol. (2001), 47(6):541-544.

Zhou, et al.; "Determination of two major metabolites of the novel anti-tumor agent 5, 6-dimethylxanthenone-4-acetic acid in hepatic microsomal incubations by high-performance liquid chromatography with fluorescence detection"; J. Chromatography B (1999), 734(1):129-136.

Zhou, et al.; "Identification of the Human Liver Cytochrome P450 Isoenzyme Responsible for the 6-Methylhydroxylation of the Novel Anticancer Drug 5, 6-Dimethylxanthenone-4-Acetic Acid"; Drug Metabolism and Disposition (2000), 28(12):1449-1456.

Zhou, et al.; "In vitro and in vivo kinetic interactions of the antitumour agent 5, 6-dimethylxanthenone-4-acetic acid with thalidomide and diclofenac"; Cancer Chemother. Pharmacol; (2001), 47(4):319-326.

Zitvogel, et al.; "Interleukin-12 and B7.1 co-stimulation cooperate in the induction of effective antitumor immunity and therapy of established tumors"; Eur. J. Immunol. (1996), 26:1335-1341.

Zwi, et al.; "Blood Flow Failure as a Major Determinant in the Antitumor Action of Flavone Acetic Acid"; J. Natl. Cancer Inst. (1989), 81:1005-1013.

Zwi, et al.; "Necrosis in non-tumour tissues caused by flavone acetic acid and 5,6-dimethyl xanthenone acetic acid"; Br. J. Cancer (1990), 62(6): 932-934.

Zwi, et al.; "The Morphological Effects of the Anti-Tumor Agents Flavone Acetic Acid and 5,6-Dimethyl Xanthenone Acetic Acid on the Colon 38 Mouse Tumor"; Pathology (1994), 26(2):161-169.

Zwi, et al.; "Correlation between immune and vascular activities of xanthenone acetic acid antitumor agents"; Oncol. Res. (1994), 6(2):79-85.

Antisoma. "AACR presentation highlights possible new cancer targets for Antisoma's DMXAA"; Press release of Antisoma plc.; Jul. 14, 2003.

Kelland, et al.; "Single Agent Activity and Potentiation of the Antitumor Activity of Paclitaxel and Gemcitabine with the Vascular Targeting Agent, 5,6-dimethylxanethenone-4-acetic acid (DMXAA) in Human Tumour Xenografts"; (poster) Jul. 13, 2003.

Gaolin, et al., "Developments in research on cancer therapy with tumor vascular endothelial cell", Article Ref. No. 0258-879X; (2000) 10-0987-04; (English Translation of "Development of the Study on the Anti-cancer Treatment against Endothelial Cells of Blood Vessel of Tumors", Zhang Li and Liu Gaolin, Academic Journal of Second Military Medical University, 21(10), 2000, 987.

Arends, et al., "A phase II study of raltitrexed and gemcitabine in patients with advanced pancreatic carcinoma", *British Journal of Cancer*, 92(3):445-448 (2005).

Come, et al., "Phase II study to evaluate combining gemcitabine with flutamide in advanced pancreatic cancer patients", *British Journal of Cancer*, 87(7):716-719 (2002).

Gridelli, et al., "Chemotherapy for Elderly Patients With Advanced Non-Small-Cell Lung Cancer: The Multicenter Italian Lung Cancer in the Elderly Study (MILES) Phase III Randomized Trial", *Journal of the National Cancer Institute*, 95(5):362-372 (2003).

Hill, et al., "Anti-Vascular Approaches To Solid Tumour Therapy: Evaluation of Vinblastine and Flavone Acetic Acid", *Int. J. Cancer*, 63:119-123 (1995).

Jordan, et al., "Comparison of the Effects of Vinblastine, Vincristine, Vindesine, and Vinepidine on Microtubule Dynamics and Cell Proliferation in Vitro", *Cancer Research*, 45:2741-2747 (1985).

Larsen, et al., "From DNA damage to G2 arrest : the many roles of topoisomerase II", *Progress in Cell Cycle Research*, 5:295-300 (2003).

Onn, et al., "Treatment of non-small-cell lung cancer a perspective on the recent advances and the experience with gefitinib", *British Journal of Cancer*, 91(Suppl. 2):S11-617 (2004).

Peters, et al., "Basis for effective combination cancer chemotherapy with antimetabolites", *Pharmacology & Therapeutics*, 87:227-253 (2000).

PTCL Safety Glossary: Structure-Activity Relationship, ptcl.chem. ox.ac.uk/MSDS/glossary/structure_activity_relationship.html, Jun. 27, 2003, 1 page.

Strauss, et al., "A phase I (tumour site-specific) study of carboplatin and temozolomide in patients with advanced melanoma", *British Journal of Cancer*, 89(10):1901-1905 (2003).

Ghaemmaghami, et al., "New Agents in the Treatment of Small Cell Lung Cancer", *Chest*, 113(1) Suppl.: 86S-91S (1998).

Horsman, et al., "Improving Conventional Cancer Therapy by Targeting Tumour Vasculature", *British Journal of Cancer*, 80(2) Suppl.: 90 (1999).—Abstract.

Siemann, et al., "Potentiation of Chemotherapy by Vascular Targeting Agents", *British Journal of Cancer*, 80(2) Suppl.: 90 (1999). —Abstract.

U.S. Appl. No. 10/946,833 (now U.S. Patent No. 7,462,642)—Restriction Requirement dated Mar. 5, 2007.

U.S. Appl. No. 10/946,833 (now U.S. Patent No. 7,462,642)—Non-Final Office Action dated May 22, 2007.

U.S. Appl. No. 10/946,833 (now U.S. Patent No. 7,462,642)—Final Office Action dated Nov. 5, 2007.

U.S. Appl. No. 10/790,943—Non-Final Office Action dated Nov. 10, 2004.

U.S. Appl. No. 10/790,943—Non-Final Office Action dated Jul. 29, 2005.

U.S. Appl. No. 10/790,943—Final Office Action dated Apr. 20, 2006.

U.S. Appl. No. 10/790,943—Non-Final Office Action dated Nov. 14, 2006.

U.S. Appl. No. 10/790,943—Final Office Action dated Jun. 11, 2007.

U.S. Appl. No. 10/790,943—Non-Final Office Action dated May 5, 2008.

U.S. Appl. No. 10/790,943—Final Office Action dated Dec. 22, 2008.

U.S. Appl. No. 11/592,678—Non-Final Office Action dated Aug. 14, 2008.

U.S. Appl. No. 11/592,678—Final Office Action dated Feb. 11, 2009.

U.S. Appl. No. 11/830,650—Non-Final Office Action dated Jan. 27, 2009.

U.S. Appl. No. 11/830,668—Non-Final Office Action dated Dec. 31, 2008.

U.S. Appl. No. 10/572,304—Restriction Requirement dated Dec. 11, 2007.

U.S. Appl. No. 10/572,304—Non-Final Office Action dated Jul. 16, 2008.

U.S. Appl. No. 10/572,304—Final Office Action dated Feb. 11, 2009.

U.S. Appl. No. 11/830,677—Non-Final Office Action dated Jan. 26, 2009.

Wilson, et al. "Combination of the Antivascular Agent DMXAA with Radiation and Chemotherapy", *I. J. Radiation Oncology*, 46(3):706, Feb. 2000.

U.S. Appl. No. 10/572,304-Non-final Office Action dated Jul. 24, 2009.

U.S. Appl. No. 10/946,833 (now U.S. Patent No. 7,462,642)—Advisory Action dated Feb. 7, 2008.

U.S. Appl. No. 10/946,833 (now U.S. Patent No. 7,462,642)—Notice of Allowance dated Aug. 4, 2008.

U.S. Appl. No. 10/790,943—Non-final Office Action dated May 1, 2009.

U.S. Appl. No. 10/790,943—Non-final Office Action dated Oct. 21, 2009.

U.S. Appl. No. 11/830,650—Final Office Action dated Jul. 16, 2009.

U.S. Appl. No. 11/830,668—Non-final Office Action dated May 28, 2008.

U.S. Appl. No. 11/830,668—Final Office Action dated Jul. 9, 2009.

U.S. Appl. No. 11/830,668—Advisory Action dated Sep. 29, 2009.

U.S. Appl. No. 11/830,677—Final Office Action dated Jul. 8, 2009.

U.S. Appl. No. 11/830,677—Advisory Action dated Oct. 6, 2009.

Calabresi, et al., "Antineoplastic agents," Chapter 52, in Goodman and Gilman's, The Pharmacological Basis of Therapeutics, 1990 Edition, pp. 1236-1238.

Hande, Kenneth R., "Clinical applications of anticancer drugs targeted to topoisomerase II," *Biochemica et Biophysica Acta* 1400, pp. 173-184 (1998).

Kelly, Karen, "New Chemotherapy Agents for Small Cell Lung Cancer," *Chest*, 117(4) Suppl., pp. 156S-162S (2000).

Lassen, et al, "Superiority of cisplatin or carboplatin in combination with teniposide and vincristine in the induction chemotherapy of small-cell lung cancer. A randomized trial with 5 years follow up," *Annals of Oncology*, 7:365-371 (1996).

Sasaki, Tsuneo, "Biochemical modulation," *Progress of Medical Science*, 164(5):251-254 (1993) (English Abstract provided.).

\* cited by examiner

ANTI-CANCER COMBINATIONS

RELATED APPLICATIONS

This application is a continuation of U.S. application Ser. No. 10/790,943, filed Mar. 2, 2004, which claims priority under 35 U.S.C. §120 to PCT Application Serial PCT/GB02/04025, filed Sep. 3, 2002, which claims priority under 35 U.S.C. §119 to Great Britain Application Serial No. 0121285.1, filed Sep. 3, 2001, the entirety of which is incorporated herein by reference.

FIELD OF THE INVENTION

The invention relates to compositions comprising combinations of anti-cancer drugs and methods of using the compositions for the treatment of cancer.

BACKGROUND 5,6-dimethylxanthenone-4-acetic acid (DMXAA) is represented by the following formula:

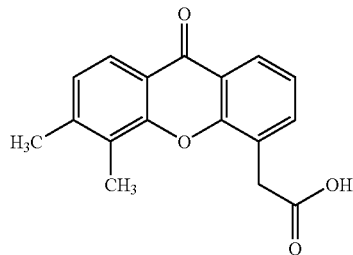

Phase I clinical trials of DMXAA have recently been completed, with dynamic MRI (Magnetic Resonance Imaging) showing that it induces a significant reduction in tumour blood flow at well-tolerated doses. DMXAA is thus one of the first antivascular agents for which activity (irreversible inhibition of tumour blood flow) has been documented in human tumours. These findings are in agreement with preclinical studies using tumours or human tumour xenografts which showed that its antivascular activity produced prolonged inhibition of tumour blood flow leading to extensive regions of haemorrhagic necrosis. However, in such studies tumours rapidly regrow from surviving cells in the well-perfused periphery. The transient tumour growth inhibition seen in most preclinical models is consistent with the lack of tumour regressions seen in the phase I clinical studies, and suggests that DMXAA is unlikely to have clinical utility as a single agent.

SUMMARY

The invention relates to combinations comprising anti-cancer agents including DMXAA and at least one of a compound selected from platinum compounds, vinca alkaloids, alkylating agents, anthracyclines, topoisomerase I inhibitors, antimetabolites and topoisomerase II inhibitors. In one embodiment, the invention provides for methods of using the combinations of the invention for treating cancer. In another embodiment the invention provides for compositions comprising the combinations of the invention. In another embodiment, the invention provides for pharmaceutical formulations comprising the combinations of the invention. The invention further provides for methods of preparing the combinations of the invention.

Thus, in a first aspect, the present invention provides a method for treating cancer, which comprises administering to a mammal, including a human, in need of such treatment an effective amount of DMXAA or a pharmaceutically acceptable salt or ester thereof and administering an effective amount of at least one of a compound selected from platinum compounds, vinca alkaloids, alkylating agents, anthracyclines, topoisomerase I inhibitors, antimetabolites and topoisomerase II inhibitors.

As used herein, "treating" means administering a therapeutically effective amount of DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors. An "effective amount" or "therapeutically effective amount" refers to a treatment regimen sufficient to decrease or ameliorate symptoms of cancer. As used herein, "decrease" refers to a decrease in the symptoms indicative of the cancer of at least 5%, preferably 5-20%, more preferably, 20-50% or most preferably, 50% or more, as compared to an untreated mammal.

"Administering" as used herein, includes but is not limited to any one of oral, topical (including dermal, buccal and sublingual), rectal and parenteral (including subcutaneous, intradermal, intramuscular and intravenous) administration, as well as administration by naso-gastric tube.

As used herein, a mammal refers to any mammal including but not limited to human, mouse, rat, sheep, monkey, goat, rabbit, hamster, horse, cow or pig.

In one embodiment, the DMXAA or a pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are administered in a potentiating ratio.

The term "potentiating ratio" is used herein to indicate that the DMXAA or pharmaceutically acceptable salt or ester thereof and the compound selected from platinum compounds, vinca alkaloids, alkylating agents, anthracyclines, topoisomerase I inhibitors, antimetabolites and topoisomerase II inhibitors are present in a ratio such that the antitumour activity of the combination is greater than that of DMXAA alone or the compound selected from platinum compounds, vinca alkaloids, alkylating agents, anthracyclines, topoisomerase I inhibitors, antimetabolites and topoisomerase II inhibitors alone or of the additive activity that would be predicted for the combinations based on the activities of the individual components in a test including but not limited to measurement of a delay in anti-tumor growth, measurement of anti-tumor activity, measurement of tumor blood flow inhibition and measurement of a decrease in tumor volume doubling or tripling (as described herein below in Examples 1 and 2). Thus the individual components act synergistically in combination provided they are present in a potentiating ratio.

As used herein, "greater" refers to at least 2-fold more, for example 2, 3, 4, 5, 10, 20, 30, 40, 50, 100, 1000-fold or more, as compared to the activity of DMXAA alone or the compound selected from platinum compounds, vinca alkaloids, alkylating agents, anthracyclines, topoisomerase I inhibitors, antimetabolites and topoisomerase II inhibitors alone or of the additive activity that would be predicted for the combinations based on the activities of the individual components in a test including but not limited to measurement of a delay in anti-tumor growth, measurement of anti-tumor activity, measurement of tumor blood flow inhibition and measurement of a decrease in tumor volume doubling or tripling (as described herein below in Examples 1 and 2).

"Greater" also refers to an increase in activity of at least 5% (for example, 5, 6, 7, 8, 9, 10, 20, 30, 40, 50, 60, 70, 80, 90, 100% or more) as compared to the activity of DMXAA alone or the compound selected from platinum compounds, vinca alkaloids, alkylating agents, anthracyclines, topoisomerase I inhibitors, antimetabolites and topoisomerase II inhibitors alone or of the additive activity that would be predicted for the combinations based on the activities of the individual components in a test including but not limited to measurement of a delay in anti-tumor growth, measurement of anti-tumor activity, measurement of tumor blood flow inhibition and measurement of a decrease in tumor volume doubling or tripling (as described herein below in Examples 1 and 2).

A potentiating ratio, for DMXAA and antimetabolites, for example gemcitabine and 5-fluorouracil, which may be successfully used to treat cancer, is in the range 1:100 to 1:2, for example, 1:100, 1:90, 1:80, 1:70, 1:60, 1:50, 1:40, 1:30, 1:20, 1:10. 1:5, 1:2 of DMXAA:antimetabolite. Suitably, the potentiating ratio is in the range 1:75 to 1:5, for example, 1:75, 1:70, 1:65, 1:60, 1:50, 1:40, 1:30. 1:20. 1:10, 1:5. A further potentiating ratio is in the range 1:50 to 1:10, for example, 1:50, 1:40, 1:30, 1:20, 1:15, 1:10. A preferred potentiating ratio is in the range 1:30 to 1:15, for example, 1:30, 1:25, 1:20, 1:15, more preferably in the range 1:25 to 1:20, for example, 1:25, 1:24, 1:23, 1:22, 1:21, 1:20 of DMXAA:antimetabolite.

A potentiating ratio, for DMXAA and platinum compound, for example carboplatin or cisplatin, which may be successfully used to treat cancer, is in the range 20:1 to 1:20, for example, 20:1, 15:1, 10:1, 8:1, 5:1, 2:1, 1:1 or 1:2, 1:5, 1:8, 1:10, 1:15, 1:20. For example, in the case of carboplatin, a potentiating ratio which may be successfully used to treat cancer, is in the range 1:20 to 1:1 of DMXAA:carboplatin, for example, 1:20, 1:15, 1:10, 1:8, 1:5, 1:2, 1:1, 1:2, 1:5, 1:8, 1:10, 1:15, 1:20. Suitably, in the case of carboplatin the potentiating ratio is in the range 1:16 to 1:2, for example, 1:16, 1;15, 1:10, 1:8, 1:5, 1:2. A further potentiating ratio in the case of carboplatin is in the range 1:10 to 1:2, for example, 1:10, 1:8, 1:5, 1:2. A preferred potentiating ratio in the case of carboplatin is in the range 1:8 to 1:3, for example, 1:8, 1:7, 1:6, 1:5, 1:4, 1:3, more preferably in the range 1:6 to 1:4, for example, 1:6, 1:5, 1:4, of DMXAA:carboplatin. Similarly, in the case of cisplatin, a potentiating ratio, which may be successfully used to treat cancer, is in the range 20:1 to 1:1, for example, 20:1, 15:1, 10:1, 8:1, 5:1, 2:1, 1:1, of DMXAA:cisplatin. Suitably, in the case of cisplatin the potentiating ratio is in the range 10:1 to 1:1, for example 10:1, 8:1, 5:1, 2:1, 1:1. A further potentiating ratio in the case of cisplatin is in the range 8:1 to 1:1, for example, 8:1, 7:1, 6:1, 5:1, 4:1, 3:1, 2:1, 1:1. A preferred potentiating ratio in the case of cisplatin is in the range 6:1 to 2:1, for example 6:1, 5:1, 4:1, 3:1, 2:1, more preferably in the range 4:1 to 2:1, for example 4:1, 3:1, 2:1, of DMXAA:cisplatin.

A potentiating ratio, for DMXAA and alkylating agents, for example cyclophosphamide, which may be successfully used to treat cancer, is in the range 1:100 to 1:2, for example, 1:100, 1:90, 1:80, 1:70, 1:60, 1:50, 1:40, 1:30, 1:20, 1:10. 1:5, 1:2 of DMXAA:alkylating agent. Suitably, the potentiating ratio is in the range 1:50 to 1:5, for example, 1:50, 1:40, 1:30, 1:20, 1:10. 1:5. A further potentiating ratio is in the range 1:30 to 1:5, for example, 1:30, 1:20, 1:10. 1:5. A preferred potentiating ratio is in the range 1:20 to 1:8, for example. 1:20, 1:15, 1:10. 1:9, 1:8 more preferably in the range 1:16 to 1:12, for example, 1:16, 1:15, 1:14, 1:13, 1:12, of DMXAA:alkylating agent.

A potentiating ratio, for DMXAA and topoisomerase II inhibitors, for example etoposide, which may be successfully used to treat cancer, is in the range 10:1 to 1:10, for example, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 of DMXAA:topoisomerase II inhibitor. Suitably, the potentiating ratio is in the range 5:1 to 1:5, for example, 5:1, 4:1, 3:1, 2:1, 1:1, 1:2, 1:3, 1:4, 1:5. A further potentiating ratio is in the range 5:1 to 1:3, for example, 5:1, 4:1, 3:1, 1:3, 1:4, 1:5. A preferred potentiating ratio is in the range 3:1 to 1:2, for example 3:1, 2:1, 1:1, 1:2, 1:3, more preferably in the range 2:1 to 1:2, for example, 2:1, 1:1, 1:2 of DMXAA:topoisomerase II inhibitor.

A potentiating ratio, for DMXAA and vinca alkaloids, for example vincristine, which may be successfully used to treat cancer, is in the range 200:1 to 5:1, for example, 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 5:1 of DMXAA:vinca alkaloid. Suitably, the potentiating ratio is in the range 150:1 to 10:1, for example, 150:1, 140:1, 130:1, 120:1, 110:1, 100:1, 90:1, 80:1, 70:1, 60:1, 50:1, 40:1, 30:1, 20:1, 15:1, 10:1. A further potentiating ratio is in the range 100:1 to 40:1. A preferred potentiating ratio is in the range 100:1 to 60:1, for example, 100:1, 90:1, 80:1, 70:1, 60:1, more preferably in the range 90:1 to 70:1, for example, 90:1, 85:1, 80:1, 75:1, 70:1, of DMXAA:vinca alkaloid.

A potentiating ratio, for DMXAA and anthracyclines, for example doxorubicin, which may be successfully used to treat cancer, is in the range 50:1 to 1:1, for example, 50:1, 40:1, 30:1, 20:1, 15:1, 10:1, 5:1, 2:1, 1:1, of DMXAA:anthracycline. Suitably, the potentiating ratio is in the range 25:1 to 1:1, for example, 25:1, 20:1, 15:1, 10:1, 5:1, 2:1, 1:1. A further potentiating ratio is in the range 16:1 to 2:1, for example, 16:1, 15:1, 10:1, 8:1, 5:1, 2:1. A preferred potentiating ratio is in the range 8:1 to 2:1, more preferably in the range 6:1 to 4:1 for example 6:1, 5:1, 4:1 of DMXAA:anthracycline.

In another aspect, the DMXAA or a pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are administered concomitantly.

As used herein, "concomitantly" refers to being administered together or simultaneously.

In another aspect, the DMXAA or a pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are administered sequentially.

As used herein, "sequentially" refers to administration in sequence, in any order, for example administration of DMXAA followed by administration of at least one of a compound selected platinum compounds, vinca alkaloids, alkylating agents, anthracyclines, topoisomerase I inhibitors, antimetabolites and topoisomerase II inhibitors. As used herein, sequential administration refers to administration of a first compound, immediately followed by administration of at least a second compound. Sequential administration also refers to administration of a first compound followed by administration of second compound, wherein there is a delay of at least 30 seconds, or more, for example, 30 seconds, 1, 5, 10, 30, 60 minutes, 2, 5, 8, 10, 24, 36, 48 or more hours, between administration of the first compound and administration of the at least a second compound.

The invention also provides for a composition comprising a combination of DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors.

In one embodiment, the DMXAA or a pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are present in a potentiating ratio.

The invention also provides for a pharmaceutical formulation comprising a combination of DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors in association with one or more pharmaceutically acceptable carriers therefor.

In one embodiment, the formulation is adapted for intravenous administration.

In one embodiment, the DMXAA or pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are present in a potentiating ratio.

The invention also provides for a process for the preparation of a composition which process comprises bringing into association a combination of DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors with one or more pharmaceutically acceptable carriers therefor.

In one embodiment, the DMXAA or pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are present in a potentiating ratio.

The invention also provides for a process for the preparation of a pharmaceutical formulation which process comprises bringing into association a combination of DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors with one or more pharmaceutically acceptable carriers therefor.

In one embodiment, the DMXAA or pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are present in a potentiating ratio.

As used herein, "bringing into association" refers to mixing, in any order the DMXAA or pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors.

The invention also provides for a kit comprising in association for separate administration DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors.

In one embodiment, the DMXAA or pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors are present in a potentiating ratio.

Examples of suitable platinum compounds are cisplatin and carboplatin.

An example of a suitable vinca alkaloid is vincristine.

An example of a suitable alkylating agent is cyclophosphamide.

An example of a suitable anthracycline is doxorubicin.

An example of a suitable topoisomerase II inhibitor is etoposide.

Examples of suitable antimetabolites are gemcitabine and 5-fluorouracil.

An example of a suitable topoisomerase I inhibitor is irinotecan.

Thus, in the present invention, the compound selected from platinum compounds, vinca alkaloids, alkylating agents, anthracyclines, topoisomerase I inhibitors, antimetabolites and topoisomerase II inhibitors may, for example, be a compound selected from carboplatin, gemcitabine, cisplatin, 5-fluorouracil, cyclophosphamide, etoposide, vincristine, doxorubicin and irinotecan.

In one embodiment of the present invention, the compound selected from platinum compounds, vinca alkaloids, alkylating agents, anthracyclines, topoisomerase I inhibitors, antimetabolites and topoisomerase II inhibitors is a compound selected from carboplatin, gemcitabine, cisplatin, 5-fluorouracil, cyclophosphamide, etoposide, vincristine and doxorubicin.

In another embodiment of the present invention, the compound selected from platinum compounds, vinca alkaloids, alkylating agents, anthracyclines, topoisomerase I inhibitors, antimetabolites and topoisomerase II inhibitors is a compound selected from carboplatin, gemcitabine, cisplatin, cyclophosphamide, etoposide, vincristine and irinotecan.

In another embodiment of the present invention, the compound selected from platinum compounds, vinca alkaloids, alkylating agents, anthracyclines, topoisomerase I inhibitors, antimetabolites and topoisomerase II inhibitors is a compound selected from carboplatin, gemcitabine, cisplatin, cyclophosphamide, etoposide and vincristine.

In another embodiment of the present invention, the compound selected from platinum compounds, vinca alkaloids, alkylating agents, anthracyclines, topoisomerase I inhibitors, antimetabolites and topoisomerase II inhibitors is a compound selected from gemcitabine, cisplatin, 5-fluorouracil, doxorubicin and irinotecan.

In another embodiment of the present invention, the compound selected from platinum compounds, vinca alkaloids, alkylating agents, anthracyclines, topoisomerase I inhibitors, antimetabolites and topoisomerase II inhibitors is a compound selected from gemcitabine, cisplatin and irinotecan.

In another embodiment of the present invention, the compound selected from platinum compounds, vinca alkaloids, alkylating agents, anthracyclines, topoisomerase I inhibitors, antimetabolites and topoisomerase II inhibitors is a compound selected from gemcitabine, cisplatin, 5-fluorouracil and doxorubicin.

In another embodiment of the present invention the DMXAA is used or is present, or the DMXAA and the compound selected from platinum compounds, vinca alkaloids, alkylating agents, anthracyclines, topoisomerase I inhibitors, antimetabolites and topoisomerase II inhibitors are used or are present, in the absence of an antibody.

In another embodiment of the present invention, when the compound selected from platinum compounds, vinca alkaloids, alkylating agents, anthracyclines, topoisomerase I inhibitors, antimetabolites and topoisomerase II inhibitors is 5-fluorouracil or doxorubicin, the DMXAA is used or is present, or the DMXAA and the compound selected from platinum compounds, vinca alkaloids, alkylating agents, anthracyclines, topoisomerase I inhibitors, antimetabolites and topoisomerase II inhibitors are used or are present, in the absence of an antibody.

DETAILED DESCRIPTION OF THE INVENTION

Figure 1:
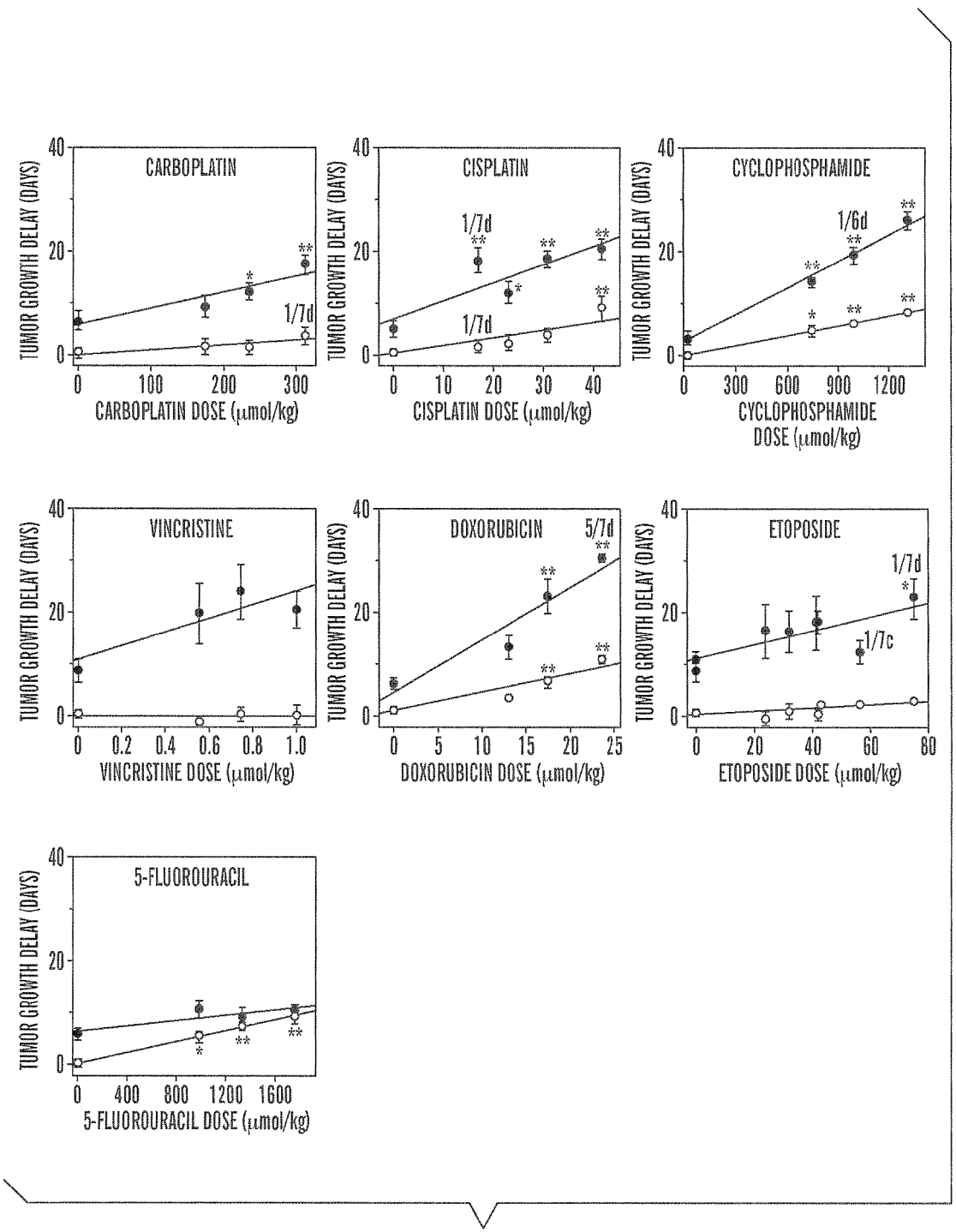
FIG. 1. Illustrates growth delay of MDAH-Mca-4 tumours after treatment of mice with chemotherapeutic drug alone (i.p.) (○) or co-administration of drug with DMXAA (80 μmol/kg) (●). Values are mean±sem for groups of 6-8 mice, ignoring deaths (d) or cures (c), the numbers of which are shown in parentheses. * and ** indicate $p<0.05$ and $<0.01$ respectively for significance of growth delay relative to corresponding control (±DMXAA).

By combining, either concomitantly or sequentially, DMXAA with a compound selected from platinum compounds, vinca alkaloids, alkylating agents, anthracyclines, topoisomerase I inhibitors, antimetabolites and topoisomerase II inhibitors, preferably with a compound selected from carboplatin, gemcitabine, cisplatin, 5-fluorouracil, cyclophosphamide, etoposide, vincristine, doxorubicin and irinotecan, potentiation of antitumour activity is achieved.

The present invention relates to either concomitantly or sequentially synergistic combinations of the compound 5,6-dimethylxanthenone-4-acetic acid (DMXAA) and a compound selected from platinum compounds, vinca alkaloids, alkylating agents, anthracyclines, topoisomerase I inhibitors, antimetabolites and topoisomerase II inhibitors, which have anti-tumour activity. Preferably, the present invention relates to synergistic combinations of the compound 5,6-dimethylxanthenone-4-acetic acid (DMXAA) and a compound selected from carboplatin, gemcitabine, cisplatin, 5-fluorouracil, cyclophosphamide, etoposide, vincristine, doxorubicin and irinotecan. More particularly, the invention relates to the use of such combinations in the treatment of cancer and pharmaceutical compositions containing such combinations.

Anti-Cancer Agents 5,6-dimethylxanthenone-4-acetic acid (DMXAA) is represented by the following formula:

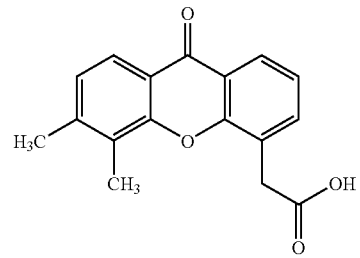

Carboplatin (Paraplatin®) is a platinum coordination cancer chemotherapeutic agent. The chemical name for carboplatin is platinum, diammine[1,1-cyclobutanedicarboxylato (2−)-0,0']-,(SP-4-2).

Cisplatin (Platinol®) is a platinum antineoplastic agent used to treat a variety of tumour types.

Gemcitabine (Gemzar®) (HCl) is a nucleotide analogue antimetabolite that exhibits antitumour activity. Gemcitabine HCl is 2'-deoxy-2',2'-difluorocytidine monohydrochloride (b-isomer).

5-fluorouracil (Adrucil®) is an injectable antineoplastic antimetabolite. Its chemical name is 5-fluoro-2,4(1H,3H)-pyrimidinedione.

Cyclophosphamide (Cytoxan®) is available as a lyophilised cake for injection or as tablets for oral use. Cyclophosphamide is a synthetic antineoplastic drug chemically related to the nitrogen mustards. The chemical name for cyclophosphamide is 2-[bis(2-chloroethyl)amino]tetrahydro-2H-13,2-oxazaphosphorine-2-oxide monohydrate.

Doxorubicin HCl (Adriamycin®) is a cytotoxic anthracycline antibiotic isolated from *Streptomyces peucetius* var. *caesius*. It has the chemical name (8S,10S)-10-[(3-amino-2, 3,6-trideoxy-a-L-lyxo-hexopyranosyl)oxy]-8-glycolyl-7,8, 9,10-tetrahydro-6,8,11-trihydroxy-1-meth-oxy-5,12-naphthacenedione hydrochloride.

Vincristine (Oncovin®, Vincasar PFS®, Vincrex®) is a vinca alkaloid antineoplastic.

Etoposide (VePesid®), (also commonly known as VP-16) is a topoisomerase II inhibitor. It is a semisynthetic derivative of podophyllotoxin. It is 4'-demethylepipodophyllotoxin-9-[4,6-0-(R)-ethylidene-(beta)-D-glucopyranoside]. Etoposide is available for oral or intravenous administration.

Irinotecan (Campto®, Camptosar®) is a topoisomerase I inhibitor. It is a semi-synthetic derivative of camptothecin. The chemical name is (S)-4,11-diethyl-3,4,12,14-tetrahydro-4-hydroxy-3,14-dioxo-1H-pyrano[3',4':6,7]-indolizinol[1,2-b]quinolin-9-yl-[1,4'-bipiperidine]-1'-carboxylate, monohydrochloride, trihydrate.

The DMXAA or pharmaceutically acceptable salt or ester thereof and the compound selected from platinum compounds, vinca alkaloids, alkylating agents, anthracyclines, topoisomerase I inhibitors, antimetabolites and topoisomerase II inhibitors may be administered concomitantly or sequentially. Preferably the DMXAA or pharmaceutically acceptable salt or ester thereof and the compound selected from platinum compounds, vinca alkaloids, alkylating agents, anthracyclines, topoisomerase I inhibitors, antimetabolites and topoisomerase II inhibitors are administered concomitantly.

Preferably the DMXAA or pharmaceutically acceptable salt or ester thereof and the compound selected from platinum compounds, vinca alkaloids, alkylating agents, anthracyclines, topoisomerase I inhibitors, antimetabolites and topoisomerase II inhibitors are present in a potentiating ratio.

Preferably the pharmaceutically acceptable salt of DMXAA is the sodium salt.

In one embodiment the compound selected from platinum compounds, vinca alkaloids, alkylating agents, anthracyclines, topoisomerase I inhibitors, antimetabolites and topoisomerase II inhibitors is carboplatin.

In one embodiment the compound selected from platinum compounds, vinca alkaloids, alkylating agents, anthracyclines, topoisomerase I inhibitors, antimetabolites and topoisomerase II inhibitors is gemcitabine.

In one embodiment the compound selected from platinum compounds, vinca alkaloids, alkylating agents, anthracyclines, topoisomerase I inhibitors, antimetabolites and topoisomerase II inhibitors is cisplatin.

In one embodiment the compound selected from platinum compounds, vinca alkaloids, alkylating agents, anthracyclines, topoisomerase I inhibitors, antimetabolites and topoisomerase II inhibitors is 5-fluorouracil.

In one embodiment the compound selected from platinum compounds, vinca alkaloids, alkylating agents, anthracyclines, topoisomerase I inhibitors, antimetabolites and topoisomerase II inhibitors is cyclophosphamide.

In one embodiment the compound selected from platinum compounds, vinca alkaloids, alkylating agents, anthracyclines, topoisomerase I inhibitors, antimetabolites and topoisomerase II inhibitors is etoposide.

In one embodiment the compound selected from platinum compounds, vinca alkaloids, alkylating agents, anthracyclines, topoisomerase I inhibitors, antimetabolites and topoisomerase II inhibitors is vincristine.

In one embodiment the compound selected from platinum compounds, vinca alkaloids, alkylating agents, anthracyclines, topoisomerase I inhibitors, antimetabolites and topoisomerase II inhibitors is doxorubicin.

In one embodiment the compound selected from platinum compounds, vinca alkaloids, alkylating agents, anthracyclines, topoisomerase I inhibitors, antimetabolites and topoisomerase II inhibitors is irinotecan.

In one embodiment, the DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II are used in a potentiating ratio, as defined herein.

Dosage and Administration

The amount of a combination of DMXAA or a pharmaceutically acceptable salt or ester thereof and the at least one of a compound selected from platinum compounds, vinca alkaloids, alkylating agents, anthracyclines, topoisomerase I inhibitors, antimetabolites and topoisomerase II inhibitors required to be effective as an anticancer agent will, of course, vary and is ultimately at the discretion of the medical practitioner. The factors to be considered include the route of administration and nature of the formulation, the mammal's bodyweight, age and general condition and the nature and severity of the disease to be treated.

Suitable DMXAA Dosage

A suitable effective dose of DMXAA, or a pharmaceutically acceptable salt thereof, for administration, either concomitantly or sequentially, with a compound selected from platinum compounds, vinca alkaloids, alkylating agents, anthracyclines, topoisomerase I inhibitors, antimetabolites and topoisomerase II inhibitors to man for the treatment of cancer is, for example, in the range of 500 to 4900 mg/m$^2$. For example, from 600 to 4900 mg/m$^2$, suitably from 600 to 3100 mg/m$^2$, more suitably from 1000 to 2500 mg/m$^2$ and particularly from 1100 to 1500 mg/m$^2$. Alternatively, the amount of DMXAA, or a pharmaceutically acceptable salt thereof, may, for example, be from 2500 to 4000 mg/m$^2$, suitably from 1200 to 3500 mg/m$^2$, more suitably from 2000 to 3000 mg/m$^2$, still more suitably from 1200 to 2500 mg/m$^2$, particularly from 2500 to 3500 mg/m$^2$, and more particularly from 2250 to 2750 mg/m$^2$. Preferably the DMXAA, or pharmaceutically acceptable salt thereof, is administered by IV once every week or every 3 weeks.

Suitable Platinum Compound Dosage

A suitable effective dose of platinum compound, for example carboplatin or cisplatin, for administration, either concomitantly or sequentially, with DMXAA, or a pharmaceutically acceptable salt thereof, to man for the treatment of cancer is, for example, in the range 10 to 500 mg/m$^2$.

Suitable Carboplatin Dosage

In the case of carboplatin a suitable effective dose for administration, either concomitantly or sequentially, with DMXAA, or a pharmaceutically acceptable salt thereof, to man for the treatment of cancer is, for example, in the range 100 to 500 mg/m$^2$. For example, from 100 to 300 mg/m$^2$, suitably from 250 to 400 mg/m$^2$, more suitably from 150 to 350 mg/m$^2$, particularly from 150 to 250 mg/m$^2$, and more particularly from 175 to 225 mg/m$^2$.

Suitable Cisplatin Dosage

Similarly, in the case of cisplatin, a suitable effective dose for administration, either concomitantly or sequentially, with DMXAA, or a pharmaceutically acceptable salt thereof, to man for the treatment of cancer is, for example, in the range 10 to 200 mg/m$^2$. For example, from 20 to 150 mg/m$^2$, suitably from 30 to 120 mg/m$^2$, more suitably from 40 to 100 mg/m$^2$, particularly from 40 to 80 mg/m$^2$, more particularly from 60 to 100 mg/m$^2$, and preferably from 75 to 100 mg/m$^2$.

Preferably the platinum compound, for example, carboplatin or cisplatin is administered by IV once every 4 weeks.

Suitable Antimetabolite Dosage

A suitable effective dose of antimetabolite, for example gemcitabine or 5-fluorouracil, for administration, either concomitantly or sequentially, with DMXAA, or a pharmaceutically acceptable salt thereof, to man for the treatment of cancer is, for example, in the range 400 to 2000 mg/m$^2$. For example, from 500 to 1500 mg/m$^2$, suitably from 600 to 1200 mg/m$^2$, more suitably from 600 to 1000 mg/m$^2$, particularly from 800 to 1200 mg/m$^2$, more particularly from 800 to 1000 mg/m$^2$, preferably from 750 to 980 mg/m$^2$, more preferably from 750 to 965 mg/m$^2$.

A suitable effective dose of antimetabolite, for example gemcitabine or 5-fluorouracil, for administration, either concomitantly or sequentially, with DMXAA, or a pharmaceutically acceptable salt thereof, to man for the treatment of cancer is, for example, in the range 2 to 20 mg/kg. For example, from 2 to 15 mg/kg, suitably from 2 to 8 mg/kg, more suitably from 6 to 12 mg/kg, particularly from 4 to 10 mg/kg, and preferably from 4 to 6 mg/kg.

Preferably the gemcitabine is administered by IV once every week and preferably the 5-fluorouracil is administered on alternate days for a period of about 2 weeks.

Suitable Alkylating Agent Dosage

A suitable effective dose of alkylating agent, for example cyclophosphamide, for administration, either concomitantly or sequentially, with DMXAA, or a pharmaceutically acceptable salt thereof, to man for the treatment of cancer is, for example, in the range 100 to 1000 mg/m$^2$. For example, from 200 to 800 mg/m$^2$, suitably from 200 to 500 mg/m$^2$, more suitably from 350 to 700 mg/m$^2$, particularly from 450 to 650 mg/m$^2$, more particularly from 500 to 600 mg/m$^2$, and preferably from 550 to 650 mg/m$^2$.

Preferably the alkylating agent, for example cyclophosphamide, is administered by IV once every 4 weeks.

Suitable Topoisomerase II Inhibitor Dosage

A suitable effective dose of topoisomerase II inhibitor, for example etoposide, for administration, either concomitantly or sequentially, with DMXAA, or a pharmaceutically acceptable salt thereof, to man for the treatment of cancer is, for example, in the range 5 to 150 mg/m$^2$. For example, from 5 to 120 mg/m$^2$, suitably from 10 to 100 mg/m$^2$, more suitably from 15 to 50 mg/m$^2$, particularly from 60 to 120 mg/m$^2$, more particularly from 35 to 75 mg/m$^2$, and preferably from 30 to 60 mg/m$^2$.

Preferably the topoisomerase II inhibitor, for example etoposide, is administered by IV daily for 4 to 7 days.

Suitable Vinca Alkaloid Dosage

A suitable effective dose of vinca alkaloid, for example vincristine, for administration, either concomitantly or sequentially, with DMXAA, or a pharmaceutically acceptable salt thereof, to man for the treatment of cancer is, for example, in the range 0.1 to 2.0 mg/m$^2$. For example, from 0.125 to 1.75 mg/m$^2$, suitably from 0.15 to 1.5 mg/m$^2$, more suitably from 0.2 to 1.4 mg/m$^2$, particularly from 0.6 to 1.4 mg/m$^2$, more particularly from 0.8 to 1.4 mg/m$^2$, and preferably from 0.5 to 1.0 mg/m$^2$.

Preferably the vinca alkaloid, for example vincristine, is administered by IV once every week.

Suitable Anthracycline Dosage

A suitable effective dose of anthracycline, for example doxorubicin, for administration, either concomitantly or sequentially, with DMXAA, or a pharmaceutically acceptable salt thereof, to man for the treatment of cancer is, for example, in the range 5 to 100 mg/m$^2$. For example, from 10 to 80 mg/m$^2$, suitably from 20 to 60 mg/m$^2$, more suitably from 40 to 75 mg/m$^2$, particularly from 20 to 50 mg/m$^2$, more particularly from 15 to 35 mg/m$^2$, and preferably from 40 to 60 mg/m$^2$.

Preferably the anthracycline, for example doxorubicin, is administered by IV once every 3-4 weeks.

The DMXAA or pharmaceutically acceptable salt or ester thereof and the compound selected from platinum compounds, vinca alkaloids, alkylating agents, anthracyclines, topoisomerase I inhibitors, antimetabolites and topoisomerase II inhibitors may be administered in any suitable form. However, for use according to the present invention the combination of DMXAA or a pharmaceutically acceptable salt or ester thereof and a compound selected from platinum compounds, vinca alkaloids, alkylating agents, anthracyclines, topoisomerase I inhibitors, antimetabolites and topoisomerase II inhibitors is preferably presented as a pharmaceutical formulation.

Pharmaceutical formulations comprise the active ingredients (that is, the combination of DMXAA or a pharmaceutically acceptable salt or ester thereof and a compound selected from platinum compounds, vinca alkaloids, alkylating agents, anthracyclines, topoisomerase I inhibitors, antimetabolites and topoisomerase II inhibitors) together with one or more pharmaceutically acceptable carriers therefor and optionally other therapeutic and/or prophylactic ingredients. The carrier(s) must be acceptable in the sense of being compatible with the other ingredients of the formula and not deleterious to the recipient thereof.

Accordingly, the present invention provides a pharmaceutical formulation comprising a combination of DMXAA or a pharmaceutically acceptable salt or ester thereof and a compound selected from platinum compounds, vinca alkaloids, alkylating agents, anthracyclines, topoisomerase I inhibitors, antimetabolites and topoisomerase II inhibitors in association with one or more pharmaceutically acceptable carriers therefor.

The present invention further provides a process for the preparation of a pharmaceutical formulation which process comprises bringing into association a combination of DMXAA or a pharmaceutically acceptable salt or ester thereof and a compound selected from platinum compounds, vinca alkaloids, alkylating agents, anthracyclines, topoisomerase I inhibitors, antimetabolites and topoisomerase II inhibitors with one or more pharmaceutically acceptable carriers therefor.

Pharmaceutical formulations include those suitable for oral, topical (including dermal, buccal and sublingual), rectal and parenteral (including subcutaneous, intradermal, intramuscular and intravenous) administration as well as administration by naso-gastric tube. The formulation may, where appropriate, be conveniently presented in discrete dosage units and may be prepared by any of the methods well known in the art of pharmacy. All methods include the step of bringing into association the active ingredients with the pharmaceutically acceptable carrier(s), for example liquid carriers or finely divided solid carriers or both, and then, if necessary, shaping the product into the desired formulation.

Preferably the pharmaceutical formulations are adapted for parenteral administration, most preferably intravenous administration. For example the compounds may be administered intravenously using formulations for each compound already known in the art.

Pharmaceutical formulations suitable for oral administration wherein the carrier is a solid are most preferably presented as unit dose formulations such as boluses, capsules or tablets each containing a predetermined amount of the active ingredients. A tablet may be made by compression or moulding, optionally with one or more accessory ingredients. Compressed tablets may be prepared by compressing in a suitable machine the active compounds in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredients, either alone or in admixture with one or more accessory ingredients, into the capsule shells and then sealing them in the usual manner. Cachets are analogous to capsules wherein the active ingredients together with any accessory ingredient(s) are sealed in a rice paper envelope. The combination of DMXAA or a pharmaceutically acceptable salt or ester thereof and a compound selected from platinum compounds, vinca alkaloids, alkylating agents, anthracyclines, topoisomerase I inhibitors, antimetabolites and topoisomerase II inhibitors may also be formulated as dispersible granules, which may for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredients are formulated in an appropriate release-controlling matrix, or are coated with a suitable release-controlling film. Such formulations may be particularly convenient for prophylactic use.

The active ingredients may also be formulated as a solution or suspension suitable for administration via a naso-gastric tube.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Pharmaceutical formulations suitable for parenteral administration include sterile solutions or suspensions of the active combination in aqueous or oleaginous vehicles. Injectable preparations may be adapted for bolus injection or continuous infusion. Such preparations are conveniently presented in unit dose or multi-dose containers which are sealed after introduction of the formulation until required for use. Alternatively, the active ingredients may be in powder form which are constituted with a suitable vehicle, such as sterile, pyrogen-free water, before use.

The pharmaceutical formulations may, for example, be in the form of liposomal formulations.

The combination of DMXAA or a pharmaceutically acceptable salt or ester thereof and compound selected from platinum compounds, vinca alkaloids, alkylating agents, anthracyclines, topoisomerase I inhibitors, antimetabolites and topoisomerase II inhibitors may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the pharmaceutical formulations for the various routes of administration described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

DMXAA may be prepared according to the methods described in Journal of Medicinal Chemistry 34(1): 217-22, January 1991 the contents of which are incorporated herein by reference.

Platinum compounds, vinca alkaloids, alkylating agents, anthracyclines, topoisomerase I inhibitors, antimetabolites and topoisomerase II inhibitors, for example, carboplatin, gemcitabine, cisplatin, 5-fluorouracil, cyclophosphamide, etoposide, vincristine, doxorubicin and irinotecan, are well known compounds and may be prepared by methods known to those skilled in the art.

It is to be understood that the present invention covers all combinations of suitable and preferred groups described hereinabove.

Cancers that may be treated in accordance with the present invention include, but are not limited to, solid tumors, for example, non-small cell lung cancers, small cell lung cancers, breast cancer, cancer of the pancreas, ovarian cancer, colorectal cancer, prostate cancer, gastric cancer, testicular cancer, bladder cancer, colonic carcinoma, parvocellular and non-parvocellular bronchial carcinoma, carcinomas of the cephalic and cervical parts, carcinomas of the thoracic and abdominal regions, cervical and endometrial carcinomas, sarcomas, melanomas, and leukemias.

Animal Models

Animal models useful according to the invention include but are not limited to the animal model of mammary carcinoma provided in Example 1, and pancreatic carcinoma provided in Example 2. Additional animal models include normal mice injected with a tumor cell line that is representative of a particular tumor or cancer type as provided herein above. Suitable tumor cell lines for the cancers recited above are available from the American Type Culture Collection (ATCC). For example, the following representative cell lines (described on the World Wide Web at ATCC.org, reference provided, incorporated herein in their entirety) are suitable for use in an animal model of the following cancers wherein an normal animal, for example a mouse is injected with the cell line provided: non-small cell lung cancers (ATCC No: CRL-5800, Name: NCI-H23); small cell lung cancers (ATCC No: CCL-257, Name NCI-H1688), breast cancer (ATCC No: HTB-132, Name: MDA-MB-468), cancer of the pancreas (ATCC No: CRL-1687, Name: BxPC-3), ovarian cancer (ATCC No: HTB-161, Name: NIH:OVCAR3), colorectal cancer (ATCC No: CCL-251, Name: NCI-H716), prostate cancer (ATCC No: CRL-1435, Name: PC-3), gastric cancer (ATCC No: CRL-1739, Name: AGS), testicular cancer (ATCC No: CRL-1973, Name: NTERA-2 cl.D1), bladder cancer (CRL-1472, Name: HT-1376), colonic carcinoma (CCL-249, Name NCI-H548), parvocellular and non-parvocellular bronchial carcinoma (ATCC No: HTB-168, Name: ChaGo-K-1), carcinomas of the cephalic and cervical parts (CRL-1594, Name: C-41), endometrial carcinomas (ATCC No: HTB-111, Name, AN3 CA), sarcomas (ATCC No: HTB-86, Name: SK-ES-1), melanomas (ATCC CRL-11147, Name: A2058), and leukemias (CRL-110423).

Kits

The invention herein also contemplates a kit format which comprises a package unit having one or more containers for separate administration of DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors. The invention provides for a kit comprising a wherein the DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors are in association with one or more pharmaceutical carriers.

The kit may also contain one or more of the following items: buffers, instructions, and controls. Kits may include containers of reagents mixed together in suitable proportions for performing the methods in accordance with the invention. Reagent containers preferably contain reagents in unit quantities that obviate measuring steps when performing the subject methods.

The DMXAA or a pharmaceutically acceptable salt or ester thereof and at least one of a compound selected from platinum compounds, vinca alkaloids, alkylating agents, anthracyclines, topoisomerase I inhibitors, antimetabolites and topoisomerase II inhibitors are provided in suitable packaging means, for example in a tube, either in solution in an appropriate buffer or in a lyophilized form.

EXAMPLES

Having now generally described the invention, the same will be more readily understood through reference to the following Examples which are provided by way of illustration, and are not intended to be limiting of the present invention, unless specified.

Example 1

DMXAA in Combination with Other Anti-Cancer Agents Demonstrates Synergistic Anti-Tumor Activity Materials and Methods Compounds: A stock solution of DMXAA, synthesised in the Auckland Cancer Society Research Centre, was prepared in phosphate-buffered saline, protected from light and stored frozen. Cisplatin (Sigma Chemical Co., St. Louis, Mo.) was dissolved in 0.9% saline. Stock solutions of carboplatin and 5-fluorouracil (Bristol Myers Squibb, Sermonita, Italy) and cyclophosphamide (Mead Johnson Oncology Products, Princeton, N.J.) were diluted with sterile water. Doxorubicin (Farmitalia Carlo Erba Pty Ltd, Clayton North, Australia), etoposide, and vincristine (Bristol-Myers Squibb, Sermonita, Italy) were diluted using 0.9% saline. All compounds were administered to mice by i.p. injection at 0.01 ml/g bodyweight.

Animals and Tumours: Murine mammary carcinoma MDAH-Mca-4 tumours were grown from stocks stored in liquid nitrogen at the sixth transplant generation. Tumours (eighth transplant generation when used) were grown from 20 μl of cell suspension (7 mg packed cells), inoculated i.m. (intra-muscular) in the right gastrocnemius muscle of female $C_3H/HeN$ mice (22-25 g at the time of treatment). Mice were randomised to treatment which commenced when the tumour+leg diameter reached 10-11 mm (0.5-0.7 g tumour).

Host Toxicity and Antitumour Activity: Mice were treated with chemotherapeutic drugs at a range of doses, at 1.33-fold increments, up to the expected MTD (maximum tolerated dose, as estimated in pilot experiments or from the literature). Toxicity was assessed as lethality, and body weight loss measured four days after treatment. Any animals becoming moribund were terminated and treated as drug-related deaths in the analysis. The diameter of the tumour-bearing leg was measured 3 times per week after treatment. Antitumour activity was assessed from the tumour growth delay, defined as the difference in time to reach the endpoint of 13 mm (1.5 g tumour) for treated and control groups. Responses were classed as cures if animals were free of evident tumour 120 days after treatment. The statistical significance of tumour growth inhibition was tested by ANOVA using SAS for Windows, with Dunnett's test to evaluate p-values for differences between treatment groups. In experiments with substantial numbers of cures (free of tumour for >120 days after treatment), statistical significance was tested by Kruskal-Wallis non-parametric analysis of variance using SAS for Windows, and the difference between treatment and control groups by Dunn's test using Sigmastat v2.0. The gradient and standard error of dose-response curves was determined by linear regression using Sigmastat, and the DMF (Dose Modifying Factor) calculated as the gradient with DMXAA/gradient without DMXAA.

Tumour blood flow inhibition: Tumour blood flow was assessed using the fluorescent perfusion marker Hoechst 33342 (8 mg/ml in saline), which was administered i.v. at various times after drug treatment. Mice were scarified 2 min later, and frozen sections (14 μm) prepared from the distal, central and proximal regions of each tumour. Sections were examined with a Nikon epifluorescence microscope at 10× magnification using a UV-1A filter block (excitation 365 nm, barrier filter 400 nm, and dichroic mirror 400 nm). A grid with 81 squares (100×100 μm), was used for point scoring of staining. The whole area of each section was scored to avoid bias between peripheral and central regions (which were less well perfused). Normal tissue was excluded but necrotic areas were included. Differences between groups were treated for significance using the Student's t-test (Sigma Stat, version-2.0; Jandel Scientific Limited).

Pharmacokinetics: Female $C_3H/HeN$ mice bearing MDAH-Mca-4 tumours (0.5-0.7 g) were injected i.p. with carboplatin (316 μmol/kg), DMXAA (80 μmol/kg), or simultaneously received carboplatin and DMXAA, at the same doses. At various times blood was collected from the retroorbital sinus of anaesthetised mice into heparinised tubes, and the plasma separated by centrifugation. Tumours were rapidly dissected and frozen at −80° C. Groups of 2-5 mice were used for each time point.

ICP-MS (Inductively coupled plasma-mass spectroscopy) analysis of platinum: Concentrations of platinum in plasma and tumours were determined using the following previously published ICP-MS method. Tumours were weighted, placed in 15 ml screw cap tubes containing 1 ml of 70% nitric acid (Riedel-de-Haen, Seelze, Germany), and left to stand overnight at room temperature. The following day, tumours were digested for 2 h at 90° C. in a sand-filled electric frying pan positioned with a fume hood. After cooling, the solubilized tumour tissues were made to volume in 10-ml volumetric flasks using Milli-Q water and then introduced into the ICP-MS. Plasma was prepared for analysis by methanol precipitation of plasma protein. Plasma was added to an equal volume of ice-cold methanol, mixed and left to stand at −20° C. for 18 h. The sample was centrifuged and an aliquot of supernatant was diluted (1:40) in 0.1% nitric acid before being introduced into the ICP-MS.

The ICP-MS system comprised a Hewlett Packard HP 4500 ICP-MS with a nickel sampling cone, Babington (v-groove) nebulizer and a Scott double-pass spray chamber maintained at 2° C. Platinum was read at 195 amu with a dwell time of 100 ms and a replicate time of 6000 ms. Calibration curves were linear ($r^2 > 0.98$) over a wide range (0.5 to 5000 ng/ml). Intra-assay and inter-assay variability and recovery were within acceptable limits. The limits of quantitation were 12.5 pg of platinum per ml of plasma and 10 ng of platinum per g of tumour tissue.

HPLC analysis of DMXAA: Concentrations of DMXAA in plasma were determined as follows. Aliquots of plasma (50 μl) were treated with 1 ml of ice-cold acetonitrile:methanol (3:1 v/v), centrifuged, and the resulting supernatants evaporated using a Speed-Vac solvent concentrator (Savant Instruments, NY). The residues were dissolved in 200 μl of 10 mM ammonium acetate buffer (pH 5) and 25 μl was analysed by HPLC using a HP1100 system with diode array detector (278 nm) and fluorescence detector. The column used was a 3.2 mm×150 mm $C_8$ 5 μm column (Alltima Associates Inc., Deerfield, Ill.) and a flow rate of 0.7 ml/min, with a mobile phase of 16% acetonitrile (v/v) in 10 mM ammonium acetate buffer (pH 5). The retention time for DMXAA was 7.3 min. Spiking of control plasma showed assay linearity from 0.1-100 μM ($r^2 = 0.999$). The intra- and inter-assay precision and accuracy gave coefficients of variation <7%, and an average recovery of 70%. The lower sensitivity limit of detection by fluorescence (signal:noise ratio of 3) was 0.1 μM.

Pharmacokinetic Modelling: Modelling of pharmacokinetic data was done using ModelMaker version 4.0 (Cherwell Scientific Limited, The Magdalen Centre, Oxford Science Park, Oxford OX4 4GA, United Kingdom). The following pharmacokinetic parameters were used: $K_{abs}$, the first-order rate constant for absorption into the central compartment; Cl, total body clearance; $Cl_{inter}$, intercompartmental clearance; $V_d$, apparent volume of distribution of the central compartment; $V_{d2}$, apparent volume of distribution of the second compartment; $K_m$, Michaelis-Menten constant; $V_{max}$, theoretical maximum rate; AUC, area under the concentration-time curve. For all compounds it was assumed that all of the administered dose would reach the central compartment (i.e. 100% bioavailability). Differences between treatment groups were tested using a F-test comparing the entire curves and if this difference was significant (i.e. $p \leq 0.05$) the estimates of each individual model parameter for both groups were tested using a 2-tailed t-test. The concentrations of free platinum and total platinum in plasma and tumour were fitted with a 1-compartment open model assuming linear pharmacokinetics. Plasma concentrations of DMXAA were fitted using a 1-compartment open model with saturable (Michaelis-Menten) elimination kinetics.

Results

Activity of DMXAA+chemotherapy drugs against MDAH-Mca-4 tumour. The antitumour activity and host toxicity of DMXAA/cytotoxic drug combinations was assessed by varying the dose of chemotherapeutic drug up to the toxicity limit, with coadministration of a fixed DMXAA dose (80 μmol/kg, ca. 80% of MTD), and evaluating subsequent tumour growth delay, as illustrated in FIG. 1. Of the seven drugs investigated, four (doxorubicin, 5-fluorouracil, cyclophosphamide and cisplatin) showed appreciable activity against this tumour as indicated by dose-response relationships providing significant slopes by linear regression, and highly significant growth delays of ca 10 days at their MTDs (which are recorded in Table 1). The other three compounds (carboplatin, etoposide and vincristine) were essentially inactive, with no individual treatment groups showing significant activity (although carboplatin gave weakly positive dose responses by linear regression).

DMXAA alone showed appreciable activity as a single agent at 80 μmol/kg, providing transient regressions and mean tumour growth delays in the range 3.5-8.3 days (overall mean 6.6±0.6 days). Co-administration of DMXAA at this dose increased the host toxicity of doxorubicin and the MTD for the chemotherapy drug was lowered by one dose level (1:33-fold) in the combination (Table 1). For the other compounds, coadministration of DMXAA did not alter the formal MTD although some additional toxicity was evident as indicated by the greater body weight loss in the combination.

In contrast to this small effect on host toxicity, co-administration of DMXAA produced a large enhancement of tumour growth delay (Table 1). The contribution of DMXAA was assessed by determining the slope of each dose-response curve by linear regression, and the DMF for DMXAA was calculated as the ratio of slopes with and without DMXAA. By this criterion the magnitude of the synergy decreased in the order vincristine >(carboplatin, cisplatin, cyclophosphamide, etoposide, doxorubicin)>5-fluorouracil. For each of these compounds, except the later, the DMF was significantly greater than unity. As an alternative criterion, the maximum tumour growth delay achievable at the MTD of the combination again indicated synergy for all the compounds with growth delays in the range 15-30 days.

Figure 2:
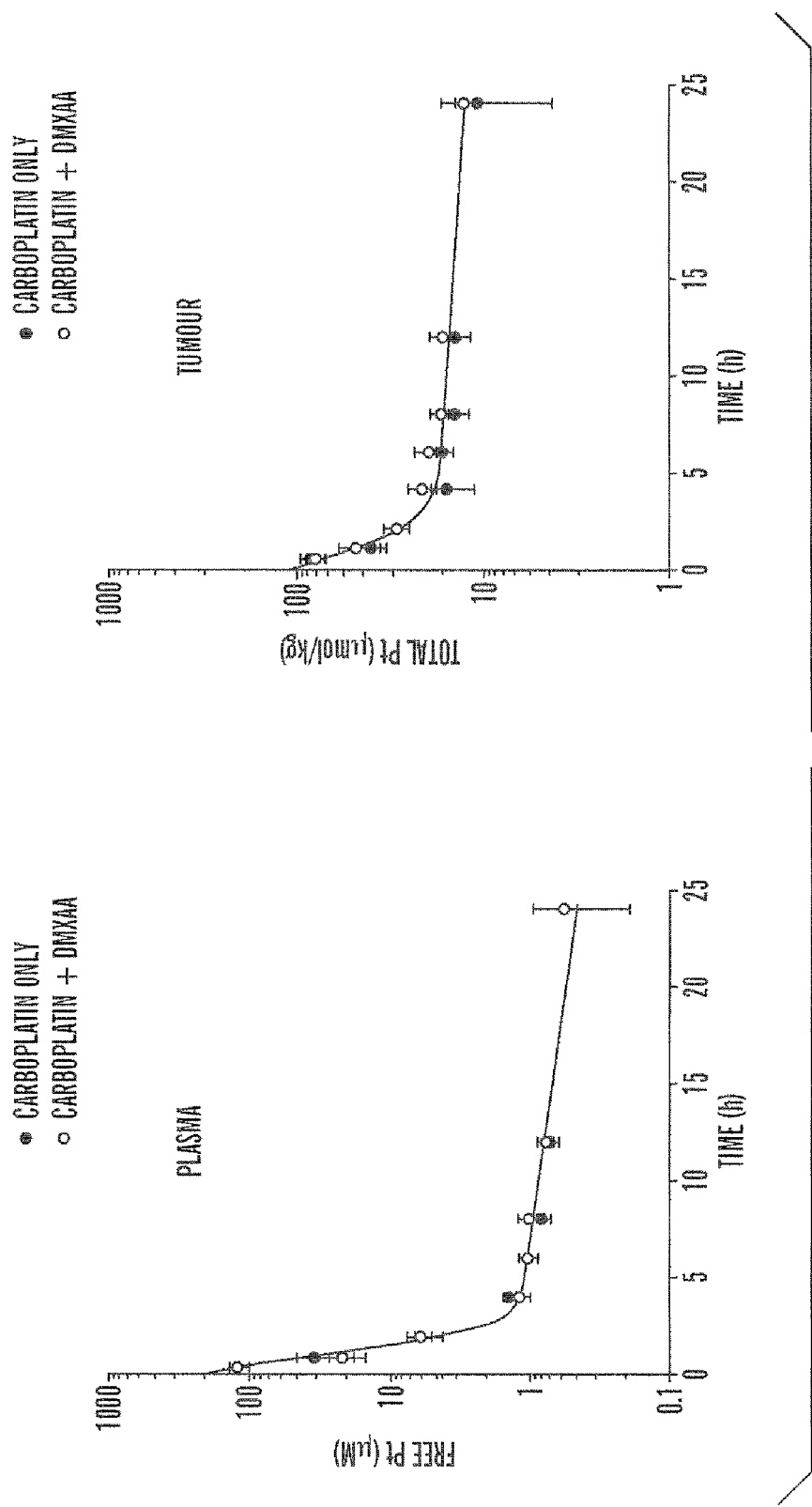
FIG. 2. Left hand panel: Plasma concentrations of free platinum following administration of carboplatin alone (316 μmol/kg) (●), or co-administered with DMXAA (80 μmol/kg) (○). Right hand panel: Tumour concentrations of total platinum following administration of carboplatin alone (316 μmol/kg) (●), or co-administered with DMXAA (80 μmol/kg) (○).

Pharmacokinetics of DMXAA and carboplatin: Studies were conducted to deduce whether a pharmacokinetic interaction underlies the synergistic therapeutic interaction between DMXAA and carboplatin. The study was conducted in $C_3H$ mice bearing MDAH-Mca-4 tumours of the same size as in the therapeutic studies. Following administration of carboplatin (316 μmol/Kg, i.p.) clearance of Pt from plasma (measured, after deproteinization, by ICP-MS) was biphasic, and was unaffected by co-administration of DMXAA (FIG. 2). Total Pt in the tumour also showed biphasic kinetics which were unaffected by co-administration of DMXAA. The lack of effect of DMXAA was confirmed by modelling the plasma with tumour pharmacokinetics as a 2-compartment open model with linear pharmacokinetics, which provided the model parameters of Table 2 and indicated that there is no significant effect of DMXAA.

This study tests the hypothesis that antivascular agents such as DMXAA have the potential to combine synergistically with conventional cytotoxic agents in the treatment of solid tumours. The early passage mammary tumour MDAH-Mca-4, used for this comparative study, was moderately refractory to most of the cytotoxic drugs tested (using single drug doses) but showed significant responses to doxorubicin, 5-fluorouracil, cyclophosphamide and cisplatin. DMXAA alone showed consistent activity as a single agent, of similar magnitude to these four agents, but neither the chemotherapy drugs nor DMXAA provided prolonged regressions or cures.

However, co-administration of DMXAA with the cytotoxic drugs caused a marked increase in response (FIG. 1). This interaction can be classified as synergistic (superadditive) on the basis of the increased slope of the cytotoxic drug dose response curve on addition of DMXAA. The interaction, quantified as the DMF (ratio of the linear regression slopes with and without DMXAA), was significantly greater than unity for all drugs except 5-fluorouracil. It is noteworthy that the interaction with DMXAA resulted in substantial activity with several compounds which did not show any single agent activity.

TABLE 1

Effect of DMXAA on host toxicity and antitumour activity of chemotherapeutic drugs against MDAH-Mca-4 tumours. Drugs were co-administered with DMXAA by i.p. injection.

| Chemotherapy drug | DMXAA (μmol/kg) | MTD (μmol/kg) | % body weight change at 4 days | Slope of dose/response (days/μmol/kg) | DMF |
|---|---|---|---|---|---|
| 5-fluorouracil | — | 1780 | −8.5 ± 0.8 | 0.0051 ± 0.001[a] | 0.5 ± 0.2 |
|  | 80 | 1780 | −14.1 ± 1.5 | 0.0027 ± 0.001 |  |
| Carboplatin | — | 316 | −5.6 ± 1.5 | 0.0094 ± 0.0035 | 3.4 ± 2.3 |
|  | 80 | 316 | −8.5 ± 1.4 | 0.032 ± 0.010 |  |
| Cisplatin | — | 42.1 | −9.5 ± 1.4 | 0.19 ± 0.06 | 1.8 ± 1.2 |
|  | 80 | 42.1 | −14.4 ± 2.3 | 0.35 ± 0.12 |  |

TABLE 1-continued

Effect of DMXAA on host toxicity and antitumour activity of chemotherapeutic drugs against MDAH-Mca-4 tumours. Drugs were co-administered with DMXAA by i.p. injection.

| Chemotherapy drug | DMXAA (μmol/kg) | MTD (μmol/kg) | % body weight change at 4 days | Slope of dose/response (days/μmol/kg) | DMF |
|---|---|---|---|---|---|
| Cyclophosphamide | — | ≧1335 | −0.8 ± 1.3 | 0.0062 ± 0.0001 | 2.7 ± 0.3 |
|  | 80 | ≧1335 | −9.2 ± 1.4 | 0.0167 ± 0.0013 |  |
| Etoposide | — | ≧75 | −2.0 ± 1.7 | 0.030 ± 0.010 | 4.7 ± 2.9 |
|  | 80 | 75(1 d) | −6.5 ± 3.3 | 0.14 ± 0.04 |  |
| Vincristine | — | 1.0 | −7.0 ± 1.2 | −0.0 ± 1.3 | >7[c] |
|  | 80 | 1.0 | −10.0 ± 1.4 | 14.1 ± 5.4 |  |
| Doxorubicin | — | 23.7 | −3.9 ± 0.6 | 0.42 ± 0.10 | 2.5 ± 1.1 |
|  | 80 | 17.8 | −5.5 ± 1.2 | 1.04 ± 0.23 |  |

[a]Standard error of the slope
[c]Estimated using upper error estimate of the slope for the chemotherapy drug only

TABLE 2

Pharmacokinetic parameters for Carboplatin (316 μmol/kg) and DMXAA (80 μmol/kg) in plasma and tumour of female C$_3$H/HeN mice bearing MDAH-Mca-4 tumours (ca 0.7 g). Numbers in parentheses are % CV.

| Parameter | Plasma | | Tumour |
|---|---|---|---|
|  | Carboplatin | DMXAA | Carboplatin |
| $K_{abs}$ (hr$^{-1}$) | 12.6 (266) | 9.3 (39) | 14.0 (286) |
| $K_m$ | — | 220 (9.2) | — |
| $V_{max}$ (μm hr$^{-1}$) | — | 63 (6.1) | — |
| Cl (1 h$^{-1}$ kg$^{-1}$) | 1.9 (41) | — | 0.28 (31) |
| Cl$_{inter}$ (1 hr$^{-1}$ kg$^{-1}$) | 0.41 (99) | — | 2.3 (24) |
| $V_d$ 1 kg$^{-1}$ | 1.0 (49) | 0.17 (1.2) | 2.7 (19) |
| $V_d$ (1 kg$^{-1}$) (coadmin.) | — | — | — |
| $V_{d2}$ (1 kg$^{-1}$) | 7.4 (227) | — | 11.3 (1163) |
| AUC (μM · hr)[a] | 112[b] | 3628[c] | 416[b] |
| AUC (μM · hr)[a] (coadmin.) | 118[b,c] | 3136[c] | 475[b,c] |

[a]AUC was calculated using the linear trapezoidal rule
[b]0-24 hours
[c]Co-administration with DMXAA
[d]0-8 hours
[e]0-30 hours Example 2

DMXAA in Combination with Gemcitabine Demonstrates Anti-Tumor Activity

Materials and Methods

Human tumour xenografts (PSN1) were established by subcutaneous injection of 5×10$^6$ cells in the right flank of female MF1 nude mice. PSN1 is a pancreatic carcinoma. Tumours were allowed to grow to a diameter of 6-8 mm before treatment (a volume of approximately 0.15 cm$^3$). Treatment groups were randomised in such a way that the mean volume in each group on the day of treatment was not statistically different. Stock solutions of DMXAA and gemcitabine (Eli Lilly & Company, Indiana) were diluted in saline and injected intravenously into tumour bearing nude mice via a lateral tail vein. For combination therapy, the two drugs were given by sequential injections into the two lateral tail veins. Control mice were untreated.

Tumours were measured in three orthogonal dimensions two to three times per week and the volume expressed as the tumour volume relative to the volume on the day of treatment. Tumours were measured until they had at least tripled in volume. The endpoint was the tumour volume tripling time.

Results

The Tables below show, in the column headed "Median", the median tumour volume tripling times for PSN1 pancreatic tumour xenografts treated with gemcitabine with or without DMXAA. The column headed "Treated—Control" shows the treated minus control tripling time, i.e. the advantage of the drug or drug combination over untreated tumours.

The gemcitabine data have been analysed as volume doubling times and tripling times. In both cases the combination of the two drugs is synergistic, the treated minus control for the combination being greater than the sum of each drug given alone.

PSN1 Volume Tripling Times (Days)

Gemcitabine Plus DMXAA

| Treatment | Median | Treated-Control |
|---|---|---|
| Control | 4.9 |  |
| 20 mg/kg DMXAA | 6.0 | 1.1 |
| 240 mg/kg gemcitabine | 13.9 | 9.0 |
| 240 mg/kg gemcitabine + 20 mg/kg DMXAA | >17 | >12 |

PSN1 Volume Doubling Times (Days)

Gemcitabine Plus DMXAA

| Treatment | Median | Treated-Control |
|---|---|---|
| Control | 3.2 |  |
| 20 mg/kg DMXAA | 3.6 | 0.4 |
| 240 mg/kg gemcitabine | 9.7 | 7.5 |
| 240 mg/kg gemcitabine + 20 mg/kg DMXAA | 15.4 | 12.2 |

Other Embodiments

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for treating breast cancer in a mammal in need of such treatment, which comprises administering an effective amount of 5,6-dimethylxanthenone-4-acetic acid (DMXAA), or a pharmaceutically acceptable salt thereof, and cyclophosphamide in a ratio in the range of 1:20 to 1:8 (DMXAA:cyclophosphamide).

2. A method according to claim 1 wherein the DMXAA or pharmaceutically acceptable salt thereof and the cyclophosphamide are administered concomitantly.

3. A method according to claim 1 wherein the DMXAA or pharmaceutically acceptable salt thereof and the cyclophsphamide are administered sequentially.

* * * * *